United States Patent
Xiang et al.

(12)

(10) Patent No.: US 11,746,142 B2
(45) Date of Patent: Sep. 5, 2023

(54) CLEAVING PRE-FUSION STATE SARS-COV-2 SPIKE PROTEIN

(71) Applicant: ABclonal Science Inc., Woburn, MA (US)

(72) Inventors: Yang Xiang, Winchester, MA (US); Yan Tan, Saugus, MA (US)

(73) Assignee: ABCLONAL SCIENCE, INC., Woburn, MA (US)

( * ) Notice: Subject to any disclaimer, the term of this patent is extended or adjusted under 35 U.S.C. 154(b) by 223 days.

(21) Appl. No.: 17/242,364

(22) Filed: Apr. 28, 2021

(65) Prior Publication Data

US 2022/0064266 A1 Mar. 3, 2022
US 2022/0227842 A9 Jul. 21, 2022

Related U.S. Application Data

(63) Continuation of application No. 17/024,392, filed on Sep. 17, 2020, now Pat. No. 11,421,019, which is a continuation-in-part of application No. 17/001,774, filed on Aug. 25, 2020, now Pat. No. 11,020,474.

(60) Provisional application No. 63/049,350, filed on Jul. 8, 2020, provisional application No. 63/044,244, filed on Jun. 25, 2020.

(51) Int. Cl.
| | |
|---|---|
| *C07K 16/10* | (2006.01) |
| *C07K 14/165* | (2006.01) |
| *C12N 15/113* | (2010.01) |
| *C12N 9/22* | (2006.01) |
| *C12N 5/071* | (2010.01) |
| *C12N 15/85* | (2006.01) |
| *G01N 33/68* | (2006.01) |

(52) U.S. Cl.
CPC ............ *C07K 16/10* (2013.01); *C07K 14/165* (2013.01); *C12N 5/0686* (2013.01); *C12N 9/22* (2013.01); *C12N 15/113* (2013.01); *C12N 15/85* (2013.01); *G01N 33/6854* (2013.01); *C12N 2310/20* (2017.05); *G01N 2333/165* (2013.01); *G01N 2800/26* (2013.01)

(58) Field of Classification Search
None
See application file for complete search history.

(56) References Cited

PUBLICATIONS

Walls et al., Cell, Apr. 2020, 181(2):281-292. (Year: 2020).*

* cited by examiner

*Primary Examiner* — Nicole Kinsey White
(74) *Attorney, Agent, or Firm* — Eric P. Mirabel, JD, LLM

(57) ABSTRACT

Disclosed is producing recombinant SARS-CoV-2 spike protein in a pre-fusion state, using furin knock out or knockdown mammalian cells (such as HEK293, CHO or other mammalian cells) and using them to generate antibodies and related binding agents. The antibodies/binding agents can be used in SARS-CoV-2 detection assays or in diagnosis of active or prior infection with SARS-CoV-2; in prophylaxis or as a therapeutic; or for prophylactic or therapeutic use against coronaviruses related to SARS-CoV-2.

1 Claim, 4 Drawing Sheets

Specification includes a Sequence Listing.

Domain organization of the SARS-CoV-2 spike protein

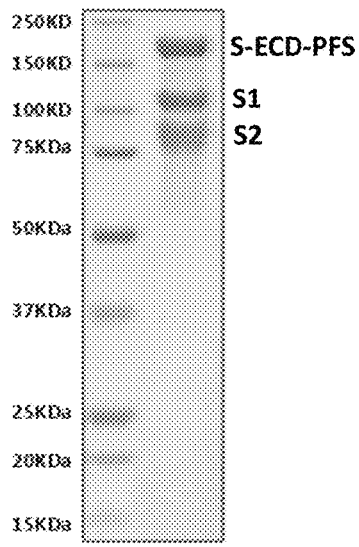
Fig. 2
Fig. 3a: Comparison of wild type FURIN gene with knockout sequence
WT-GAAGGTCTTCACCAACAC --INSERT-- ATGGGTTCCTCAACCTG (SEQ ID NO: 1)
KO-GAAGGTCTTCACCAACAC------------------ ATGGGTTCCTCAACCTG (SEQ ID NO: 2)
WT INSERT SEQUENCE:
GTGGGCTGTGCGCATCCCTGGAGGCCCAGCGGTGGCCAACAGTGTGGCACGGAAGC (SEQ ID NO: 3)
Fig. 3b. Confirming HEK293 has the knockout FURIN gene with Western Blot
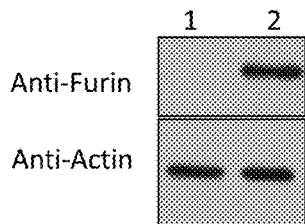

Anti-6XHis (SEQ ID NO: 4)

Fig. 4. Recombinant S-ECD-PFS generated with a single band at high yield

Fig. 5. Activity of recombinant S-ECDs and S1, measured using ACE2 binding assay
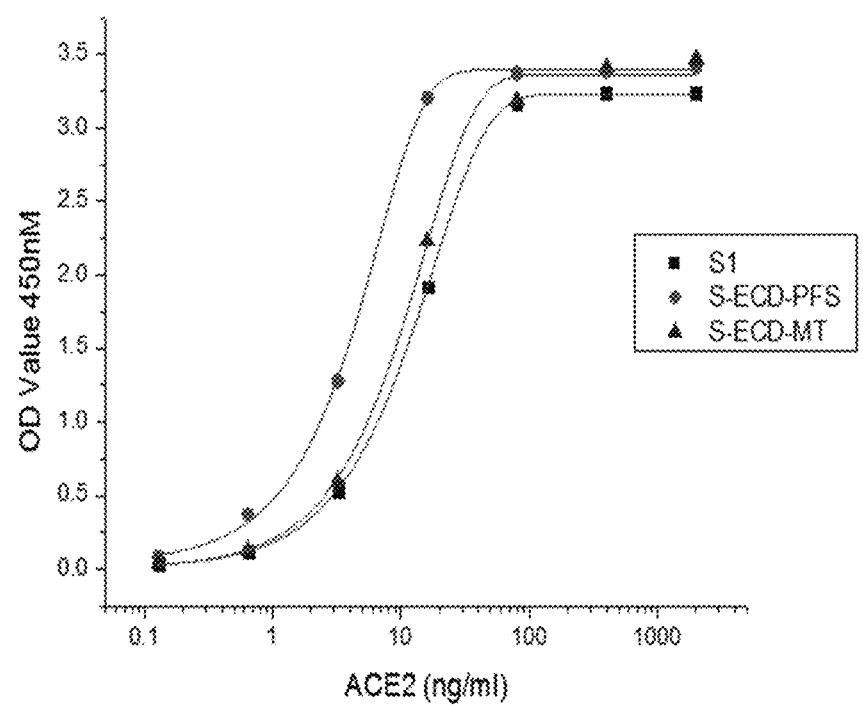

CLEAVING PRE-FUSION STATE SARS-COV-2 SPIKE PROTEIN

SEQUENCE LISTING STATEMENT

The instant application contains a Sequence Listing which has been submitted electronically in ASCII format and is hereby incorporated by reference in its entirety. Said ASCII copy, created on Oct. 21, 2020, is named AbClonalSPFS-Ab.txt and is 42,558 bytes in size.

BACKGROUND

For the coronavirus SARS-CoV-2, which is responsible for the COVID-19 pandemic, only limited treatment options having limited efficacy are available. It is known to primarily enter human cells by binding of its spike protein to the receptor angiotensin converting enzyme 2 (ACE2).

SARS-CoV-2 has four structural proteins, known as the S (spike), E (envelope), M (membrane), and N (nucleocapsid) proteins. The N protein holds the RNA genome, and the S, E, and M proteins together create the viral envelope. The spike ("5") protein is responsible for allowing the virus to attach to and fuse with the membrane of a host cell.

The S protein is a class I fusion protein; which are known to exist as trimers in their pre-fusion and post-fusion states. The S protein 51 subunit mediates cellular attachment, and the S2 subunit is involved in fusion which allows viral genome entry into the cell. The S protein has two states, a pre-fusion state and a mature/active form, achieved after proteolytic cleavage and activation.

Recombinant SARS-CoV-2 structural proteins are essential for antibody, vaccine and drug development. Recombinant wild-type S-ECD (extracellular domain) is challenging to produce and very unstable. Most of the recombinant S-ECDs on the market contain a mutation to avoid protease cleavage, making the recombinant version different from wild-type and potentially less useful in research or therapy.

Proteolytic cleavage of the S protein can occur in the constitutive secretory pathway of infected cells or during viral entry into target cells, and is essential for viral infectivity.

Furin is a processing enzyme that cleaves substrate proteins into their mature/active forms. Substrates of furin include blood clotting factors, serum proteins and growth factor receptors as well as the viral spike proteins. Furin belongs to the subtilisin-like proprotein convertase family. The members of this family are proprotein convertases that process latent precursor proteins into their biologically active products. Furin is enriched in the Golgi apparatus, where it functions to cleave other proteins into their mature/active forms. Furin is believed to be one of the proprotein convertases for the S protein.

Therefore, inhibition or disruption of cleavage of the S protein by furin may allow production of the S protein in a pre-fusion state (referred to as S-ECD-PFS). S-ECD-PFS can be used as an antigen to generate antibodies for use in detection assays or in diagnosis, or to generate antibodies and related binding agents to SARS-CoV-2 for use in passive immunization or therapy.

SUMMARY

The invention relates to using furin knock out or knockdown mammalian cells (such as HEK293, CHO or other mammalian cells) which produce recombinant SARS-CoV-2 spike protein in a pre-fusion state, to generate antibodies and related binding agents. An exemplary method of generating S-ECD-PFS and confirming its activity is summarized as follows:

1. Use a CRISPR Cas9 protocol to knock out the furin gene in mammalian cells, such as HEK293 cells;
2. Transfect expression vectors for the S-ECD gene into the furin-/- cells;
3. Purify recombinant S-ECD-PFS, preferably using a nickel column; and
4. Measure S-ECD-PFS' bio-activity, for example, by determining its binding ability to recombinant Human ACE2 in a functional ELISA.

The recombinant S-ECD-PFS can be used as an antigen to generate antibodies/binding molecules for use in detection assays (e.g., in blood or tissues for transfusion or transplantation) or in diagnosis of active or prior infection with SARS-CoV-2. The recombinant S-ECD-PFS can also be used as an antigen to generate antibodies/binding molecules to SARS-CoV-2 for use in passive immunization or other therapy, against SARS-CoV-2 or the following viruses related to SARS-CoV-2: CoV-ZXC21 (MG772934), SARSCoV (NC_004718.3), SARS-like BM4821(MG772934), HCoV-0C43 (AY391777), HKU9-1 (EF065513), HCoV-NL63 (KF530114.1), HCoV229E (KF514433.1), MERS-CoV (NC019843.3), and HKU1 (NC_006577.2).

BRIEF DESCRIPTION OF THE FIGURES

FIG. 2 illustrates the bands in the gel from proteolytic processing and separation of recombinant S-ECD-PFS when expressed in HEK293.

FIG. 3a illustrates the differences between the furin gene wild type ("WT") and the knock out gene expressed in HEK293 clones 30-18 and 30-28. The sequences shown are WT, wild type (SEQ ID NO: 1) and KO, knock out (SEQ ID NO: 2), with the WT insert separately shown (SEQ ID NO: 3).

FIG. 3b is a Western blot, showing that furin was not present in the media containing HEK293 clones 30-18 and 30-28 (right-hand column) based on absence of agglutination in the right-hand column following adding a anti-furin antibody to the media, with the left-hand column including cells expressing WT furin, and the second right-hand including anti-actin, as controls.

FIG. 4 is a gel showing media fractions (cols. 1-5) from the furin-/- cells, following protein purification with a nickel column.

FIG. 5 shows results from an ACE2 binding ELISA for the recombinant S-ECD-PFS, and for a conventional, currently marketed recombinant S-ECD.

DETAILED DESCRIPTION

Figure 1:
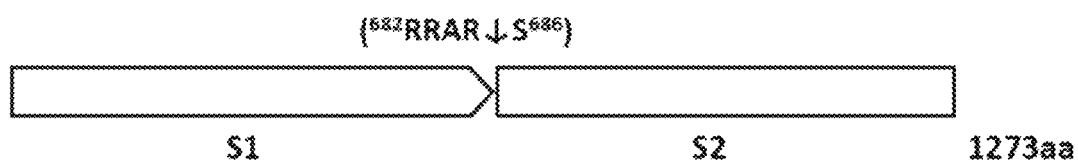
FIG. 1 depicts the domain organization of the SARS-CoV-2 spike protein and illustrates the furin cleavage site.
Figure 3C:
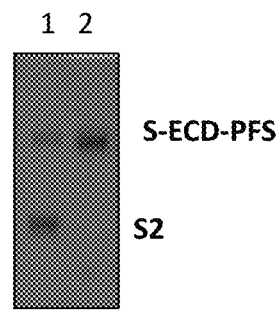
FIG. 3c is a gel showing S-ECD-PFS as a single major band (col. 2) when expressed in FURIN gene knockout HEK293 cells, with HEK293 cells expressing furin WT (col. 1) as control.
Figure 3C:
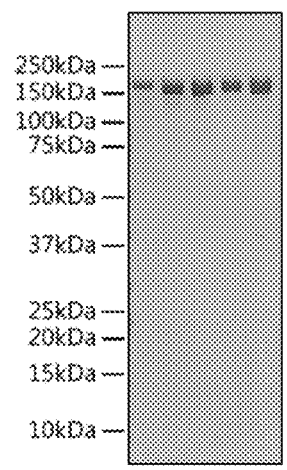

The singular forms "a", "an", and "the" include plural references unless the context clearly dictates otherwise.

A "binding agent" refers to all antibodies, antibody fragments or derivatives of antibodies as described below, as well as proteins and molecules other than proteins, antibodies and fragments or derivatives of antibodies which target S-ECD-PFS, any of which could be modified and tested to become binding agents with high affinity for S-ECD-PFS, using techniques similar to those described below.

A "conjugate" includes conjugates with antibodies or binding agents or conjugates with S-ECD-PFS, as determined from the context. A conjugate can include fusion proteins and proteins or antibodies conjugated with one or more than one polypeptide or antibody or Binding Agent, nucleic acid or chemical compound or a drug carrier. Alternatively, or in addition, a conjugate can comprise one or more other pharmaceutically active agents or drugs. Examples of such other pharmaceutically active agents or drugs that may be suitable for use in a conjugate (or included in a drug carrier) include antibiotics, known antiviral drugs, cytotoxic drugs, and other antibiotics and drugs known or suspected to inhibit or ameliorate Covid 19 infection, including hydroxychloroquine, zithromycin, Remdesivir™, nitric oxide (encapsulated), Ifenprodil, ribavirin, interferon ß-1a, interferon-α, other interferons, Recombinant *Mycobacterium bovis*, colchicine, favipiravir, lopinavir, ritonavir, Peginterferon Lambda-1A, and Fenretinide, as well as other antibiotics e.g., doxorubicin, vincristine, cisplatin, daunomycin, methotrexate and other anticancer agents such as toxins (such as diphtheria or ricin), cyclophosphamide and other medications, also can be used. alkylating agents (e.g., cyclophosphamide, melphalan etc.), cytotoxic antibiotics (doxorubicin, epirubicin, bleomycin, mitomycin, methotrexate, capecitabine, gemcitabine, fluorouracil, vinca alkaloids and etoposide (vinblastine, vincristine etc.), platinum compounds (carboplatin, cisplatin, oxaliplatin), taxanes (paclitaxel, docetaxel, etc.), topoisomerase I inhibitors (irinotecan, topotecan, etc.) as well as agents like cyclophosphamide, and combinations thereof. In one embodiment, the composition can comprise one or more polypeptide (antibody), fusion protein, conjugate, nucleic acid, vector, or cell of the invention and one or more other pharmaceutically active agents or drugs.

A "conservative amino acid substitution" is one in which the amino acid residue is replaced with an amino acid residue having a similar side chain Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "drug carrier" includes liposomes, polymeric micelles, microspheres and nanoparticles.

The term "linker" refers to a compound or moiety that acts as a molecular bridge to operably link two different molecules (e.g., wherein one portion of the linker binds to a binding agent, and wherein another portion of the linker binds to the other molecule(s) in the conjugate). Linkers include, but are not limited to, chemical chains, chemical compounds (e.g., reagents), amino acids, and the like. The linkers may include, but are not limited to, homobifunctional linkers, hetero-bifunctional linkers, biostable linkers, and biodegradable linkers. The linker may be non-planar (e.g., so that the bound components in the conjugate are not rigidly fixed). Heterobifunctional linkers, contain one end having a first reactive functionality to specifically link a first molecule, and an opposite end having a second reactive functionality to specifically link to a second molecule. Depending on such factors as the molecules to be linked, and the conditions in which the linking is performed, the linker may vary in length and composition for optimizing such properties as preservation of biological function stability, resistance to certain chemical and/or temperature parameters, and of sufficient stereo-selectivity or size. Preferably the linker is a "synthetic peptidic linker" that is designated to be rich in glycine, glutamine, and/or serine residues. These residues are arranged e.g. in small repetitive units of up to five amino acids. This small repetitive unit may be repeated for two to five times to form a multimeric unit. At the amino- and/or carboxy-terminal ends of the multimeric unit up to six additional arbitrary, naturally occurring amino acids may be added.

The term S-ECD-PFS refers to SEQ ID NO: 16 and in the context of preparation of antibodies/binding agents for therapy, prophylaxis or in detection assays, is to be read as including other related proteins used in the same way as such antibodies/binding agents, including antibodies/binding agents made using the techniques described herein against any of: CoV-ZXC21 (MG772934), SARSCoV (NC_004718.3), SARS-like BM4821(MG772934), HCoV-0C43 (AY391777), HKU9-1 (EF065513), HCoV-NL63 (KF530114.1), HCoV229E (KF514433.1), MERS-CoV (NC019843.3), HKU1 (NC_006577.2).

The term "sequence identity" refers to the identical amino acids in two sequences compared; such that they can range from 0 to 100% sequence identity. In some embodiments, the sequence identity of a related protein can be about 75%, 80%, 85%, 90%, 91%, 92%, 93%, 94%, 95%, 96%, 97%, 98% or 99% sequence identity with S-ECD-PFS or the antibodies/binding agents against it.

Binding Agents

The invention includes antibodies (polyclonal and monoclonal) and other binding agents targeting S-ECD-PFS, administered for diagnosis, prophylaxis or therapy of SARS-CoV-2 or related pathogen infection, or for detection of SARS-CoV-2 or related pathogens in blood units or tissue samples, or in forensic applications, including disease monitoring.

Typically, an antibody has a heavy and light chain. Each heavy and light chain contains a constant region and a variable region (VH and VL, respectively). The regions are also known as "domains." Light and heavy chain variable regions contain a "framework" region interrupted by three hypervariable regions, also called "complementarity-determining regions" or "CDRs." The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found.

In one preferred embodiment, an anti-S-ECD-PFS monoclonal antibody (usually generated in mice or other rodents) or a fragment thereof, is a chimeric, humanized, or human monoclonal antibody. Generally, a humanized antibody has one or more amino acid residues introduced into it from a source that is non-human. These non-human amino acid residues are often referred to as import residues, which are typically taken from an import variable domain. Humanization can be essentially performed following the methods described in Jones et al., Nature 321: 522-525 (1986); Riechmann et al., Nature 332: 323-327 (1988); or Verhoeyen et al., Science 239: 1534-1536 (1988), by substituting rodent CDRs or CDR sequences for the corresponding sequences of a human antibody. Accordingly, such humanized antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

In some embodiments, "human antibody" refers to an immunoglobulin comprising human hypervariable regions in addition to human framework and constant regions. Such antibodies can be produced using various techniques known in the art. For example in vitro methods involve use of recombinant libraries of human antibody fragments displayed on bacteriophage (e.g., McCafferty et al, 1990, Nature 348: 552-554; Hoogenboom & Winter, J. Mol. Biol. 227: 381(1991); and Marks et al, J. Mol. Biol. 222: 581 (1991)), yeast cells (Boder and Wittrup, 1997, Nat Biotechnol 15: 553-557), or ribosomes (Hanes and Pluckthun, 1997, Proc Natl Acad Sci USA 94: 4937-4942). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 6,150,584, 5,545,807; 5,545,806; 5,569,825; 5,625,126; 5,633,425; 5,661,016, and in the following scientific publications: (e.g., Jakobavits, Drug Deliv Rev. 31: 33-42 (1998), Marks et al, Bio/Technology 10: 779-783 (1992); Lonberg et al, Nature 368: 856-859 (1994); Morrison, Nature 368: 812-13 (1994); Fishwild et al, Nature Biotechnology 14: 845-51 (1996); Neuberger, Nature Biotechnology 14: 826 (1996); Lonberg &Huszar, Intern. Rev. Immunol. 13: 65-93 (1995).

In certain embodiments, the antibody or the fragment thereof disclosed herein comprises or is an F(ab)'2, a Fab, an Fv, or a single-chain Fv fragment of the above anti-S-ECD-PFS antibodies.

In some embodiments, "antibody fragments" means molecules that comprise a portion of an intact antibody, generally the antigen binding or variable region of the intact antibody. Examples of antibody fragments include Fab, Fab', F(ab)'2, and Fv fragments; single domain antibodies (see, e.g., Wesolowski, Med Microbiol Immunol. (2009) 198 (3): 157-74; Saerens, et al., Curr Opin Pharmacol. (2008) 8 (5): 600-8; Harmsen and de Haard, Appl Microbiol Biotechnol. (2007) 77 (1): 13-22)); helix-stabilized antibodies (see, e.g., Arndt et al., J Mol Biol 312: 221-228 (2001); diabodies (see below); single-chain antibody molecules ("scFvs," see, e.g., U.S. Pat. No. 5,888,773); disulfide stabilized antibodies ("dsFvs", see, e.g., U.S. Pat. Nos. 5,747,654 and 6,558,672), and domain antibodies ("dAbs," see, e.g., Holt et al., Trends Biotech 21(11): 484-490 (2003), Ghahroudi et al., FEBS Lett. 414: 521-526 (1997), Lauwereys et al., EMBO J 17: 3512-3520 (1998), Reiter et al., J. Mol. Biol. 290: 685-698 (1999), Davies and Riechmann, Biotechnology, 13: 475-479 (2001)).

U.S. Pat. No. 5,932,448 discloses making of bispecific antibodies with Fab' portions joined by a leucine zipper; U.S. Pat. No. 7,538,196, discloses making of bispecific antibodies where portions are joined with a linker; U.S. Pat. No. 8,148,496 discloses a multi-specific Fv antibody construct having at least four variable domains which are linked with each other via peptide linkers. A bispecific antibody could have one arm targeting ICB and the other arm targeting a tumor or cancer marker.

US Publ'n No. 20170335281 describes making of a genetically modified T cell expressing a CAR that comprises an antigen binding domain that binds to a cancer associated antigen. The same general techniques can be applied to modify T cells or other immune effector cells to express one or more of CDR1, CDR2 and CDR3 of an antigen binding domain, for cancer treatment. The antigen binding domain of the CAR polypeptide molecule can include any antibody, antibody fragment, an scFv, a Fv, a Fab, a (Fab')$_2$, a single domain antibody (SDAB, disclosed in WO 9404678 and Hamers-Casterman, C. et al. (1993) Nature 363:446-448), a VH or VL domain, or a VHH domain. Such CAR expressing T cells could be used in combination with the therapy described herein, or the antigen binding domain could be an anti-S-ECD-PFS domain.

High Affinity Antibody Variants

Making of Anti-S-ECD-PFS Antibodies with High Affinity

Antibodies can be humanized with retention of high affinity for the antigen and other favorable biological properties. To achieve this goal, humanized antibodies are prepared by a process of analysis of the parental sequences and various conceptual humanized products using three-dimensional models of the parental and humanized sequences. Three-dimensional immunoglobulin models are commonly available. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved.

Examples of framework region residues to modify include those which non-covalently bind target directly (Amit et al. Science 233: 747-753 (1986)); interact with/effect the conformation of CDR (Chothia et al. J. Mol. Biol. 196: 901-917 (1987)); and/or participate in the VL-VH interface (EP 239 400 B1). In certain embodiments, modification of one or more of such framework region residues results in an enhancement of the binding affinity of the antibody for the target of interest.

Nucleic acid molecules encoding amino acid sequence variants are prepared by a variety of methods known in the art. These methods include, but are not limited to, oligonucleotide-mediated (or site-directed) mutagenesis, PCR mutagenesis, and cassette mutagenesis of an earlier prepared variant or a non-variant version of the species-dependent antibody. The preferred method for generating variants is an oligonucleotide-mediated synthesis. In certain embodiments, the antibody variant will only have a single hypervariable region residue substituted, e.g. from about two to about fifteen hypervariable region substitutions.

One method for generating the library of variants is by oligonucleotide mediated synthesis. Three oligonucleotides of approximately 100 nucleotides each may be synthesized spanning the entire light chain or heavy chain variable region. Each oligonucleotide may comprise: (1) a 60 amino acid stretch generated by the triplet (NNK)20 where N is any nucleotide and K is G or T, and (2) an approximately 15-30 nucleotide overlap with either the next oligo or with the vector sequence at each end. Upon annealing of these three oligonucleotides in a PCR reaction, the polymerase will fill in the opposite strand generating a complete double stranded heavy chain or light chain variable region sequence. The number of triplets may be adjusted to any length of repeats and their position within the oligonucleotide may be chosen so as to only substitute amino acids in a given CDR or framework region. By using (NNK), all twenty amino acids are possible at each position in the encoded variants. The overlapping sequence of 5-10 amino acids (15-30 nucleotides) will not be substituted, but this may be chosen to fall within the stacking regions of the framework, or may substituted by a separate or subsequent round of synthesis. Methods for synthesizing oligonucleotides are well known in the art and are also commercially available. Methods for generating the antibody variants from these oligonucleotides are also well known in the art, e.g., PCR.

The library of heavy and light chain variants, differing at random positions in their sequence, can be constructed in any expression vector, such as a bacteriophage, each of which contains DNA encoding a particular heavy and light chain variant.

Following production of the antibody variants, the biological activity of variant relative to the parent antibody is determined. As noted above, this involves determining the binding affinity of the variant for the ICB target. Numerous high-throughput methods exist for rapidly screening antibody variants for their ability to bind the target of interest.

One or more of the antibody variants selected from this initial screen may then be screened for enhanced binding affinity relative to the parent antibody. One common method for determining binding affinity is by assessing the association and dissociation rate constants using a BIAcore surface plasmon resonance system (BIAcore, Inc.). A biosensor chip is activated for covalent coupling of the target according to the manufacturer's (BIAcore) instructions. The target is then diluted and injected over the chip to obtain a signal in response units (RU) of immobilized material. Since the signal in RU is proportional to the mass of immobilized material, this represents a range of immobilized target densities on the matrix. Dissociation data are fit to a one-site model to obtain koff+/−s.d. (standard deviation of measurements). Pseudo-first order rate constant (ks) are calculated for each association curve, and plotted as a function of protein concentration to obtain kon+/−s.e. (standard error of fit). Equilibrium dissociation constants for binding, Kd's, are calculated from SPR measurements as koff/kon. Since the equilibrium dissociation constant, Kd, is inversely proportional to koff, an estimate of affinity improvement can be made assuming the association rate (kon) is a constant for all variants.

The resulting candidate(s) with high affinity may optionally be subjected to one or more further biological activity assays to confirm that the antibody variant(s) with enhanced binding affinity still retain the desired therapeutic attributes, as can be tested in the assays described in the figures above. The optimal antibody variant retains the ability to bind the ICB target with a binding affinity significantly higher than the parent antibody. The antibody variant(s) so selected may be subjected to further modifications oftentimes depending upon the intended use of the antibody. Such modifications may involve further alteration of the amino acid sequence, fusion to heterologous polypeptide(s) and/or covalent modifications such as those elaborated below. For example, any cysteine residues not involved in maintaining the proper conformation of the antibody variant may be substituted, generally with serine, to improve the oxidative stability of the molecule and prevent aberrant cross linking. Conversely, (a) cysteine bond(s) may be added to the antibody to improve its stability (particularly where the antibody is an antibody fragment such as an Fv fragment).

Conjugates of Binding Agents

Conjugates of binding agents with any cytotoxic agents, antibiotics, known antiviral drugs, cytotoxic drugs, and other antibiotics and drugs known or suspected to inhibit or ameliorate Covid 19 infection noted above, as well as with drug carriers containing any such cytotoxic agents, antibiotics, etc., can be used in therapy or prophylaxis of Covid 19.

Such binding agents and methods of conjugating the binding agents to a molecule of interest are well known in the art and have been used in the production of antibody conjugates. Some examples of linking groups and conjugation methods are described in US Publication No. 2011/0060318 (incorporated by reference). The choice of binding agent, coupling (conjugation) technique and linking group for use in the conjugates described herein is well known.

Binding agents are conjugated via reactive sites on the binding agents via a linking group. For example, primary amino groups present on amino acid residue such as the epsilon amino group of lysine, and the alpha amino group of N-terminal amino acids of proteins can be used as functional groups for conjugation. Often it is desirable to convert one or more primary amino groups of a binding agent to a thiol-containing group (e.g., from a cysteine or homocysteine residue), an electrophilic unsaturated group such as a maleimide group, or halogenated group such as a bromoacetyl group, for conjugation to thiol reactive peptides. Optionally, a primary amino group on the hemagglutinin FIR peptide or on a linker moiety attached to the peptide, can be converted to the thiol-containing group, for coupling with a thiol (sulfhydryl) moiety on the carrier protein, e.g., by a disulfide bond.

In some embodiments, the conjugation can be achieved, for example, by using succinimidyl 4-[N-maleimidomethyl] cyclohexane-1-carboxylate (SMCC), sulfosuccinimidyl 4-(N-maleimidomethyl)cyclohexane-1-carboxylate (sSMCC €-€- -maleimidocaproyloxy]-sulfosuccinimde ester (sEMCS), bis-diazobenzidine (BDB), N-maleimidobenzoyl-N-hydroxysuccinimide ester (MBS), glutaraldehyde, 1-ethyl-3-(3-dimethylaminopropyl) carbodiimide (EDCI), or N-acetyl homocysteine thiolactone (NAHT).

In the SMCC method, SMCC cross-links the SH-group of a cysteine residue to the amino group of a lysine residue on the binding agent. In the SMCC method, the binding agent first is activated by reacting SMCC with a primary amine (e.g., on a lysine residue of the carrier protein). The resulting activated binding agent is then separated from any excess SMCC and by-product therefrom, and a cysteine-containing peptide is added. The thiol group of the cysteine adds across the double bond of the maleimide moiety of the SMCC-derivatized binding agent, thus forming a covalent sulfide bond to couple the binding agent to the peptide. If a hemagglutinin FIR peptide does not include a cysteine residue, then a cysteine residue should be added to the peptide, preferably at the N-terminus or C-terminus. If the epitope portion of the hemagglutinin FIR peptide contains a cysteine or if there is more than one cysteine group in the peptide, then another conjugation technique that does not modify the cysteine residues should be utilized. Since the linkage between the binding agent and the peptide should not interfere with the epitope portion of the peptide, the added cysteine residue optionally can be separated from the hemagglutinin FIR peptide by including one or more amino acid residues as a spacer. The cysteine, spacer residues, and the modified SMCC attached to the binding agent constitute the linking group of the hemagglutinin FIR peptide conjugate.

Another simple coupling of a peptide to a binding agent can be achieved with a carbodiimide crosslinker such as 1-ethyl-3-(3-dimethylaminopropyl) carbodiimide hydrochloride (EDC), 1-cyclohexyl-2-(2-morpholinoethyl) carbodiimide metho-p-toluenesulfonate (CMC), and the like to covalently attach carboxyl groups to primary amine groups. This method is simple and provides a relatively random orientation that allows for antibody generation against many possible epitopes. One drawback is that EDC coupling can result in some amount of polymerization. This can decrease the solubility of the conjugate, which can complicate the handling of the material.

Other coupling agents can be used to conjugate the FIR peptide to the binding agent, either directly or via a linking group. For example, conjugation can be achieved using isocyanate coupling agents, such as 2-morpholinoethylisocyanide; N-acetyl homocysteine thiolactone, which can be used to add a thiol group onto a binding agent such as OMPC coupling with a maleimide or bromoacetyl functionalized peptide; or any other agents for coupling haptens (potential immunogens) to polypeptides and proteins, many of which are well known.

Non-specific cross-linking agents and their use are well known in the art. Examples of such reagents and their use include reaction with glutaraldehyde; reaction with N-ethyl-N'-(3-dimethylaminopropyl)carbodiimide, with or without admixture of a succinylated carrier; periodate oxidation of glycosylated substituents followed by coupling to free amino groups of a protein carrier in the presence of sodium borohydride or sodium cyanoborohydride; periodate oxidation of non-acylated terminal serine and threonine residues forming terminal aldehydes which can then be reacted with amines or hydrazides creating a Schiff base or a hydrazone, which can be reduced with cyanoborohydride to secondary amines; diazotization of aromatic amino groups followed by coupling on tyrosine side chain residues of the protein; reaction with isocyanates; or reaction of mixed anhydrides. The linkers can be supplemented and extended with spacer groups, such as additional amino acid residues, adipic acid dihydrazide, and the like.

Typical spacer peptide groups for use in conjugation of the FIR peptide to the binding agent include single amino acids (e.g., Cys) and short peptide sequences (i.e., short non-hemagglutinin FIR peptide sequences) attached to the FIR peptide, e.g., a lysine containing peptide, a cysteine-containing peptide, and the like. Some preferred linking groups comprise a sulfide bond (e.g., as in SMCC and related coupling methods). Some preferred linking groups include a Cys residue bound to the succinimido moiety through the sulfhydryl side chain thereof which is bound the N-terminus of the FIR peptide by a peptide bond. The 1-carbonyl group on the cyclohexyl moiety of Formula I is bound to a primary amine on the binding agent by an amide bond.

In some embodiments, the peptide conjugates include a single hemagglutinin FIR peptide attached to the binding agent, while in other embodiments, two or more hemagglutinin FIR peptides can be attached to the binding agent.

Formulations for In Vivo Use

I. Dosing of the Binding Agents and Other Active Ingredients

1. Formulations

The dosages of binding agents or conjugates for treating or prophylaxis of SARS-CoV2 can be determined as follows. The conjugates can include polyethylene glycol, immunoglobulin Fc fragments, or collagen, albumin and other proteins which are linked to a base molecule, and antibodies (including monoclonal antibodies and fragments thereof). Any composition or compound that can simulate the biological response associated with the binding of ACE-2 receptors can be used. General details on techniques for formulation and administration are well-described in the scientific literature (see, e.g., Remington's Pharmaceutical Sciences, Maack Publishing Co., Easton Pa.).

The formulations containing pharmaceutically active products used in the methods of the disclosure can be formulated for administration in any conventionally acceptable way including, but not limited to, intravenously, subcutaneously, intramuscularly, sublingually, topically, orally and via inhalation. Illustrative examples are set forth below.

When the formulations are delivered by intravenous injection, the formulations containing pharmaceutically active ligands can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a nontoxic parenterally-acceptable diluent or solvent. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, capsules, liquids, lozenges, gels, syrups, slurries, suspensions, etc., suitable for ingestion by the patient, which would often include an enteric coating to prevent destruction of the ligand in the highly acidic environment of the stomach. Pharmaceutical preparations for oral use can be combinations of ligands with a solid excipient, optionally grinding a resulting mixture, and processing the mixture of granules, after adding suitable additional compounds, if desired, to obtain tablets or pills.

Suitable solid excipients are carbohydrate or protein fillers which include, but are not limited to, sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate. Pharmaceutical preparations that can also be used orally are, for example, push-fit capsules made of gelatin, as well as soft, sealed capsules made of gelatin and a coating such as glycerol or sorbitol. Push-fit capsules can contain ligands mixed with a filler or binders such as lactose or starches, lubricants such as talc or magnesium stearate, and, optionally, stabilizers. In soft capsules, the ligands may be dissolved or suspended in suitable liquids, such as fatty oils, liquid paraffin, or liquid polyethylene glycol with or without stabilizers.

Aqueous suspensions for internal use contain ligands mixed with excipients suitable for the manufacture of aqueous suspensions. Such excipients include a suspending agent, such as sodium carboxymethylcellulose, methylcellulose, hydroxypropylnethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, and other additives as desired, including coloring agents, flavoring agents and sweetening agents, such as sucrose, aspartame or saccharin. Formulations can be adjusted for osmolarity.

Oil suspensions for internal use can be formulated by suspending ligands in a vegetable oil, such as arachis oil, olive oil, sesame oil or coconut oil, or in a mineral oil such as liquid paraffin. The oil suspensions can contain a thickening agent, such as beeswax, hard paraffin or cetyl alcohol. Sweetening agents can be added to provide a palatable oral preparation. These formulations can be preserved by the addition of an antioxidant such as ascorbic acid.

Dispersible powders and granules of the disclosure suitable for preparation of an aqueous suspension by the addition of water can be formulated from ligands in admixture with a dispersing, suspending and/or wetting agent, and one or more preservatives. Suitable dispersing or wetting agents and suspending agents include those disclosed above. Additional excipients, for example sweetening, flavoring and coloring agents, can also be present.

The pharmaceutical formulations can also be in the form of oil-in-water emulsions. The oily phase can be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening and flavoring agents. Syrups and elixirs can be formulated with sweetening agents, such as glycerol, sorbitol or sucrose. Such formulations can also contain a demulcent, a preservative, a flavoring or a coloring agent.

For intravenous injection, water soluble antibodies can be administered by the drip method, whereby a pharmaceutical formulation containing the formulation and a physiologically acceptable excipients is infused. Physiologically acceptable excipients may include, for example, 5% dextrose, 0.9% saline, Ringer's solution or other suitable excipients.

In one embodiment, the formulation is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts, and stents or other implantable devices, site specific carriers, direct injection, or direct application. See, e.g., WO 00/53211 and U.S. Pat. No. 5,981,568.

In another embodiment of the present disclosure, an article of manufacture is provided which contains any of the pharmaceutical compositions and formulations described herein (e.g., comprising a binding agent) and provides instructions for its use and/or reconstitution. The article of manufacture comprises a container. Suitable containers include, for example, bottles, vials (e.g. dual chamber vials), syringes (such as dual chamber syringes) and test tubes. The container may be formed from a variety of materials such as glass or plastic. The container holds the formulation and the label on, or associated with, the container may indicate directions for reconstitution and/or use. For example, the label may indicate that the formulation is reconstituted to particular protein concentrations. The container holding the formulation may be a multi-use vial, which allows for repeat administrations (e.g., from 2-6 administrations) of the reconstituted formulation. The article of manufacture may further comprise a second container comprising a suitable diluent (e.g. BWFI). Upon mixing of the diluent and the lyophilized formulation, the final protein concentration in the reconstituted formulation will generally be at least 50 mg/mL. The article of manufacture may further include other materials desirable from a commercial and user standpoint, including other buffers, diluents, filters, needles, syringes, and package inserts with instructions for use.

2. Administration and Dosing Regimen of the Formulations

The formulations containing pharmaceutically active binding agent and other active ingredients can be administered in any conventionally acceptable way including, but not limited to, by intravenous, intramuscular, intraperitoneal, intracerebrospinal, subcutaneous, intracutaneous, intraarticular, intrasynovial, intrathecal, intradermal, intratumoral, intranodal, intramedulla, oral, inhalation or topical routes; or it may be administered orally, by inhalation spray, topically, rectally, nasally, buccally, vaginally or via an implanted reservoir; and in any case, as a bolus or by continuous infusion over a period of time; or via injectable depot routes of administration such as using 1-, 3-, or 6-month depot injectable or biodegradable materials and methods Administration will vary with the pharmacokinetics and other properties of the drugs and the patient's condition.

Commercially available nebulizers for liquid formulations, including jet nebulizers and ultrasonic nebulizers are useful for administration. Liquid formulations can be directly nebulized and lyophilized powder can be nebulized after reconstitution. Alternatively, binding agents can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice, and rats.

The amount of binding agent alone or in combination with another agent that is adequate to accomplish this is considered the therapeutically effective dose. The dosing schedule and amounts, i.e., the "dosing regimen," will depend upon a variety of factors, including the stage of the disease or condition, the severity of the disease or condition, the severity of the adverse side effects, the general state of the patient's health, the patient's physical status, age and the like. In calculating the dosage regimen for a patient, the mode of administration is also taken into consideration. The dosing regimen must also take into consideration the pharmacokinetics, i.e., the rate of absorption, bioavailability, metabolism, clearance, and the like. Based on these values (which are determined in vitro, and in mammalian animal models and extrapolated to humans) the dosing regimen is projected for humans, and is then tested and further refined in clinical trials, in a conventional dose-finding study, as is well-known in the art.

The state of the art allows the clinician to determine the dosing regimen for each individual patient, depending on factors including administration route, disease stage, patient size, and patient level of SARS-CoV2 or related pathogen. For example, a physician may initially use escalating dosages, starting at a particular level, and then titrate the dosage at increments for each individual being treated based on their individual responses. Depending on the subject, the administration of the formulation is maintained for as specific period of time or for as long as needed to effectively treat the subject's symptoms or prevent their occurrence in the first place.

Lyophilized Formulation

After preparation of a suitable binding agent or conjugate, it can be prepared in a formulation for administration to a subject. A lyophilized formulation is especially preferred for the binding agent, which as a first step, requires preparing a pre-lyophilized formulation. The amount of binding agent in the pre-lyophilized formulation is determined taking into account the desired dose volumes, mode(s) of administration etc. The binding agent is generally present in solution. For example, the binding agent may be present in a pH-buffered solution at a pH from about 4-8, and preferably from about 5-7. Exemplary buffers include histidine, phosphate, Tris, citrate, succinate and other organic acids. The buffer concentration can be from about 1 mM to about 20 mM, or from about 3 mM to about 15 mM, depending, for example, on the buffer and the desired isotonicity of the formulation (e.g. of the reconstituted formulation). The preferred buffer is histidine as it can have lyoprotective properties. Succinate is also a useful buffer.

The lyoprotectant is added to the pre-lyophilized formulation. In preferred embodiments, the lyoprotectant is a non-reducing sugar such as sucrose or trehalose. The amount of lyoprotectant in the pre-lyophilized formulation is generally such that, upon reconstitution, the resulting formulation will be isotonic, as preferred, though hypertonic reconstituted formulations may also be suitable. In addition, the amount of lyoprotectant must not be too low such that an unacceptable amount of degradation/aggregation of the Binding Agent occurs upon lyophilization.

Where the lyoprotectant is a sugar (such as sucrose or trehalose) and the binding agent is an antibody, exemplary lyoprotectant concentrations in the pre-lyophilized formulation are from about 10 mM to about 400 mM, and preferably from about 30 mM to 5 about 300 mM, and most preferably from about 50 mM to about 100 mM.

The ratio of binding agent to lyoprotectant is selected for each binding agent and lyoprotectant combination. In the case of an antibody as the binding agent and a sugar (e.g., sucrose or trehalose) as the lyoprotectant for generating an isotonic reconstituted formulation with a high protein concentration, the molar ratio of lyoprotectant to antibody may be from about 100 to about 1500 moles lyoprotectant to 1 mole antibody, and preferably from about 200 to about 1000 moles of lyoprotectant to 1 mole antibody, including from about 200 to about 600 moles of lyoprotectant to 1 mole antibody.

In preferred embodiments, it has been found to be desirable to add a surfactant to the pre-lyophilized formulation. Alternatively, or in addition, the surfactant may be added to the lyophilized formulation and/or the reconstituted formulation. Exemplary surfactants include nonionic surfactants such as polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palnidopropyl-, or isostearamidopropyl-betaine (e.g lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethyl glycol, polypropyl glycol, and copolymers of ethylene and propylene glycol (e.g. Pluronics, PF68). The amount of surfactant added is such that it reduces aggregation of the reconstituted protein and minimizes the formation of particulates after reconstitution. For example, the surfactant may be present in the pre-lyophilized formulation in an amount from about 0.001-0.5%, and preferably from about 0.005-0.05%.

A mixture of the lyoprotectant (such as sucrose or trehalose) and a bulking agent (e.g. mannitol or glycine) may be used in the preparation of the pre-lyophilization formulation. The bulking agent may allow for the production of a uniform lyophilized cake without excessive pockets therein.

Other pharmaceutically acceptable carriers, excipients or stabilizers such as those described in Remington's Pharmaceutical Sciences 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include; additional buffering agents; preservatives; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The pharmaceutical compositions and formulations described herein are preferably stable, so as to retain its physical and chemical stability and integrity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for protein, at about 120° C. for about 30 minutes.

After the binding agent and lyoprotectant are mixed together, the formulation is lyophilized. Many different freeze-dryers are available for this purpose such as Hull50®

(Hull, USA) or GT20® (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation.

Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g. 40-60 hrs). A secondary drying stage may be carried out at about 0-40° C., depending primarily on the type and size of container and the type of protein employed. For example, the shelf temperature throughout the entire water removal phase of lyophilization may be from about 15-30° C. (e.g., about 20° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g. 10-15 hours). The pressure may be the same as that employed during the primary drying step. Freeze-drying conditions can be varied depending on the formulation and vial size.

In some instances, it may be desirable to lyophilize the protein formulation in the container in which reconstitution of the protein is to be carried out in order to avoid a transfer step. The container in this instance may, for example, be a 3, 5, 10, 20, 50 or 100 cc vial. As a general proposition, lyophilization will result in a lyophilized formulation in which the moisture content thereof is less than about 5%, and preferably less than about 3%.

At the desired stage, typically when it is time to administer the formulation to the patient, the lyophilized formulation may be reconstituted with a diluent such that the Binding Agent concentration in the reconstituted formulation is preferably similar to that of the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%.

Alternatively, a non-lyophilized formulation may be used, including a binding agent, and any of the well-known carriers, excipients, buffers, stabilizers, preservatives, adjuvants and other additives described herein and well known in the art.

Detection Assays

Provided methods permit detection of complex formation between a binding agent and S-ECD-PFS. Detection of the complexes may be achieved by any available method, e.g., an enzyme-linked immunosorbent assay (ELISA). For example, in some embodiments, an antibody to S-ECD-PFS is used. In some embodiments, a secondary antibody, e.g., an anti-S-ECD-PFS antibody is used. One or more antibodies may be coupled to a detection moiety. In some embodiments, a detection moiety is or comprises a fluorophore. As used herein, the term "fluorophore" (also referred to as "fluorescent label" or "fluorescent dye") refers to moieties that absorb light energy at a defined excitation wavelength and emit light energy at a different wavelength. In some embodiments, a detection moiety is or comprises an enzyme. In some embodiments, an enzyme is one (e.g., ß-galactosidase) that produces a colored product from a colorless substrate.

As used herein, the terms "measuring" or "measurement," or alternatively "detecting" or "detection," means assessing the presence, absence, quantity or amount (which can be an effective amount) of a substance within a sample, including the derivation of qualitative or quantitative concentration levels of such substances, or otherwise evaluating the values or categorization of a subject's.

In some embodiments, a test is performed by adding capture agent to a substrate, e.g., a reaction vessel, under conditions such that the capture agent binds to the substrate, e.g., using an ELISA. A sample, e.g., tissue sample from a subject, blood, plasma, saliva or tears, may be added to the capture-agent containing substrate in a reaction vessel. Any capture agent-binding molecules present may bind to the immobilized capture agent molecules. An antibody or an antibody-detection agent conjugate may be added to the reaction mixture. The antibody part of the conjugate binds to any antigen molecules, creating an antibody-antigen-antibody "sandwich." After washing away any unbound conjugate, a substrate solution may be added to aid in detection. For example, after a set interval, the reaction may be stopped (e.g., by adding 1 N NaOH) and the concentration of colored product formed may be measured in a spectrophotometer. The intensity of color is proportional to the concentration of bound antigen.

EXAMPLES AND EXPERIMENTS

It has been predicted the S protein contains a furin cleavage site between $R^{682}$ and $S^{686}$ ($^{682}RRAR{\downarrow}S^{686}$), as shown in FIG. 1. The following experiments were carried out to verify furin's role in S protein cleavage.

S-ECD is Proteolytically Cleaved into Three Bands in Wild-Type HEK293 Cells

To generate recombinant S-ECD proteins for uses in antibody development, first, a recombinant S-ECD having a 6-member Histamine tag protein at the C terminus ("5-ECD-C6×His") was produced in HEK293 cells, then purified using a nickel column. Three bands were observed for the wild-type S-ECD-C6×His following expression, purification and separation using SDS-PAGE. As predicted, the results indicated that the S protein contains a furin cleavage site between amino acid R682 and amino acid S686 ($^{682}RRAR{\downarrow}S^{686}$). See FIG. 1. As shown in FIG. 2, the 180 KD band corresponds to S-ECD-PFS and the 120 KD and 80 KD bands seem to correspond to the mature/active form of the S protein containing the S1 and S2 subunits.

However, the yield was low and the protein is not stable. The yield of S-ECD in HEK293 wild-type cells is generally much lower (less than 1 mg/1). Most of the recombinant S-ECDs on the market (referred to as S-ECD-MT) has a mutated cleavage site region, as shown in FIG. 1 ($^{682}$RAAA↓S$^{686}$), in order to generate a product mimicking S-ECD-PFS, and to thereby avoid protease cleavage. However, the artificial mutation/deletion also generated an irrelevant epitope and is potentially less useful in research or therapy. In addition, because of the mutation, the conventional recombinant protein is not suitable for further processing to generate an active form of furin.

Generation of Furin Gene KO Cells in HEK293 Cells by CRISPR

On the hypothesis that knocking out the FURIN gene in HEK293 cells and then expressing S-ECD in the KO in HEK293 cells would generate an intact furin protein, CRISPR-Cas9 was employed to generate the KO HEK293 cells. Two sgRNAs were designed to target exon 1. Single clones were selected and the genomic DNA was sequenced and analyzed. Two clones were sequenced which both had a 56 bp deletion resulting in a frame-shift. The KO and WT sequences of furin in the relevant regions are depicted in FIG. 3*a*.

Furin protein was assayed by Western Blot; and as expected, was no longer present in the media from the KO HEK293 cells, as shown in FIG. 3*b*.

Increased Yield of S-ECD in HEK293 FURIN Gene KO Cells

The same construct of the S-ECD gene generating S-ECD-C6×His was transfected into HEK293 wild type and Furin−/− cells. The conditioned media containing S-ECD-C6×His was separated by SDS-PAGE and detected by Western Blot, using an anti-6×His antibody. As expected, recombinant S-ECD showed two bands in HEK293 wild type cells, one being the full-length S-ECD and the other being S2, whereas recombinant S-ECD showed a single band in furin−/− cells. Result are shown in FIG. 3*c*.

To scale up the culture and transfection in furin−/− cells, conditioned media was collected to 1 L and proteins were purified with a nickel column. The yield of S-ECD-PFS was much higher in furin−/− cells compared with wild type HEK293 cells (>20 mg/l culture). Results are shown in FIG. 4.

S-ECD-PFS has Higher ACE2 Binding Affinity than S-ECD-MT

An enzyme-linked immunosorbent assay (ELISA) was used to measure and quantify the binding activity between the S-ECDs or recombinant S1 and ACE2.

Recombinant S-ECDs and recombinant S1 (as a control) were immobilized at 2 μg/mL (100 μL/well) to a 96 well plate. Recombinant ACE2 with an added Fc domain was added to the wells by 5-fold serial dilution, from 2 μg/mL (100/well), 6 times, and a blank was used as a negative control. Captured recombinant ACE2-Fc was measured by anti-human Fc-HRP antibody. The OD was measured and the EC50 was calculated by Origin8 software. The EC50 of S1 was 12.14 ng/mL. The EC50 of S-ECD-MT was 10.38 ng/mL. The EC50 of S-ECD-PFS was 4.33 ng/mL. Lower EC50 indicates the increased binding activity, as shown in FIG. 5.

These results indicate S-ECD-PFS has higher affinity and is superior to S1 or S-ECD-MT for use as an antigen to generate antibodies or for use in detection assays or in diagnosis, as a therapeutic to interfere with SARS-CoV-2 cellular binding, or as a vaccine (to generate antibodies to SARS-CoV-2).

DETAILED METHODS

The CRISPR Cas9 protocol used the following sgRNAs:

```
sgRNA1:
                                  (SEQ ID NO: 19)
GATGCGCACAGCCCACGTGT sgRNA2:
                                  (SEQ ID NO: 20)
ACAGTGTGGCACGGAAGCAT
``` incorporated into in the vector: £°PX459£¬addgene #62988 (from Addgene, Watertown Mass.) at the Bbs1 site. The forward and reverse sgRNA constructs (with vectors) are shown below:

```
Vector-sgRNA1 (forward):
                                  (SEQ ID NO: 5)
£°CACC-GATGCGCACAGCCCACGTGT Vector-sgRNA1 (reverse):
                                  (SEQ ID NO: 6)
£°AAAC-ACACGTGGGCTGTGCGCATC Vector-sgRNA2 (forward):
                                  (SEQ ID NO: 7)
£°CACC-ACAGTGTGGCACGGAAGCAT Vector-sgRNA2 (reverse):
                                  (SEQ ID NO: 8)
£°AAAC-ATGCTTCCGTGCCACACTGT
```

For mammalian cell transfection and protein purification, plasmid preparation was in accordance with the following exemplary protocol.

Plasmids all carry a betalactamase (amp) resistance gene and are grown in *E. coli* at 37° C. (or 30° C.) in shaker flasks overnight. High quality plasmid DNA can be obtained using commercially available Maxiprep kits (Qiagen), preferably including an endotoxin removal step.

HEK293 cells were adapted to Expi293 Expression Medium. The media and transfection agents below were used in a standard protocol with the equipment below, but other cell lines (including 293T, CHO etc.) with other media and transfection reagents can also be used.

Materials and Equipment

Expi293 Expression Medium (Gibco #A1435102)

Opti-MEM I Reduced Serum Medium (Gibco #31985088)

ExpiFectamine 293 Transfection Kit (Gibco #A14524)

PBS (1×) (Gibco #10010-023 or equivalent)

Ni-NTA Agarose (Qiagen #30230 or equivalent)

NuPAGE 4-12% Bis-Tris Protein Gels (Invitrogen Catalog number: NP0329BOX)

SDS-PAGE cell and power supply

Sodium Chloride NaCl (Sigma-Aldrich #S3014 or equivalent)

Imidazole (Sigma-Aldrich #I5513 or equivalent)

Furin mAb antibody (Abclonal A5043)

Actin mAb antibody (Abclonal AC026)

Recombinant S-ECD R683A, R685A mutation (Abclonal RP01260MT)

Recombinant ACE2 (Abclonal RP01275)

Purification was performed with a nickel column (though other protein purification methods can also be used).

Sequences
Wild type FURIN gene locus: part of NCBI Reference Sequence: NC_000015.10

(SEQ ID NO: 9)

cctgcccgtctcggccccatgcccccaccagtcagccccgggccacaggcagtgagcaggcacctgggagccgaggc cctgtgaccaggccaaggagacgggcgctccagggtcccagccacctgtccccccatggagctgaggccctggagct atgggtggtagcagcaacaggaaccaggtcctgctagcagctgatgctcagggccagaaggtcttcaccaacacgtggg ctgtgcgcatccctggaggcccagcggtggccaacagtgtggcacggaagcatgggacctcaacctgggccaggtagg tgaccccacaggacactgccaggggtgggaccagagaagacagggattctgggagcaggagctgaggccttgatg ctcaggggcatctgggtagccggcatgactgggtggccatgagcaaagcacaggtggttcaggcaagcagca FURIN gene genomic sequencing primers
seq-F :

(SEQ ID NO: 10)

TCCTCTCAGGGTCGGCACTC, seq-R :

(SEQ ID NO: 11)

GCTGCTTGCCTGAACCACCT

FURIN gene locus after KO (SEQ ID NO: 12)

cgtctcggccccatgcccccaccagtcagccccgggccacaggcagtgagcaggcacctgggagccgaggccctgtg accaggccaaggagacgggcgctccagggtcccagccacctgtccccccatggagctgaggccctggagctatgggt ggtagcagcaacaggaaccaggtcctgctagcagctgatgctcagggccagaaggtatcaccaacacatggggacctca acctgggccaggtaggtgaccccacaggacactgccaggggtgggaccagagaagacagggattctgggagcag gagctgttggccttgtttgctcaggggcatctgggtagccggcatgttctgggtggccatgagcaaagcacaggtggttca ggcaagcagca Furin-WT-protein sequence (SEQ ID NO: 13)

MELRPWLLWVVAATGTLVLLAADAQGQKVFTNTWAVRIPGGPAVANSVARK

HGFLNLGQIFGDYYHFWHRGVTKRSLSPHRPRHSRLQREPQVQWLEQQVAK

RRTKRDVYQEPTDPKFPQQWYLSGVTQRDLNVKAAWAQGYTGHGIVVSILD

DGIEKNHPDLAGNYDPGASFDVNDQDPDPQPRYTQMNDNRHGTRCAGEVAA

VANNGVCGVGVAYNARIGGVRMLDGEVTDAVEARSLGLNPNHIHIYSASWGP

EDDGKTVDGPARLAEEAFFRGVSQGRGGLGSIFVWASGNGGREHDSCNCDG

YTNSIYTLSISSATQFGNVPWYSEACSSTLATTYSSGNQNEKQIVTTDLRQKCT

ESHTGTSASAPLAAGIIALTLEANKNLTWRDMQHLVVQTSKPAHLNANDWAT

NGVGRKVSHSYGYGLLDAGAMVALAQNWTTVAPQRKCIIDILTEPKDIGKRL

EVRKTVTACLGEPNHITRLEHAQARLTLSYNRRGDLAIHLVSPMGTRSTLLAA

RPHDYSADGFNDWAFMTTHSWDEDPSGEWVLEIENTSEANNYGTLTKFTLVL

YGTAPEGLPVPPESSGCKTLTSSQACVVCEEGFSLHQKSCVQHCPPGFAPQVL

DTHYSTENDVETIRASVCAPCHASCATCQGPALTDCLSCPSHASLDPVEQTCS

RQSQSSRESPPQQQPPRLPPEVEAGQRLRAGLLPSHLPEVVAGLSCAFIVLVFV

TVFLVLQLRSGFSFRGVKVYTMDRGLISYKGLPPEAWQEECPSDSEEDEGRGE

RTAFIKDQSAL

Furin-Mutation-protein sequence
MELRPWLLWVVAATGTLVLLAADAQGQKVFTNTW (SEQ ID NO: 14)* frame shift S-ECD coding sequence
S-ECD (AA Val16-Gln1208 (SEQ ID NO: 15)) subcloned into pcDNA vector by
5'XbaI/3'AgeI, after optimization (Accession #YP_009724390.1)
gtgaacctgaccaccaggacccaacttcctcctgcctacaccaactcctcaccaggggagtctactaccctgacaaggtgt tcaggtcctctgtgctgcacagcacccaggacctgttcctgccattcttcagcaatgtgacctggttccatgccatccatgtgt -continued

```
ctggcaccaatggcaccaagaggtttgacaaccctgtgctgccattcaatgatggagtctactttgccagcacagagaaga gcaacatcatcaggggctggattttttggcaccaccctggacagcaagacccagtccctgctgattgtgaacaatgccacca atgtggtgattaaggtgtgtgagttccagttctgtaatgacccattcctgggagtctactaccacaagaacaacaagtcctgg atggagtctgagttcagggtctactcctctgccaacaactgtacctttgaatatgtgagccaaccattcctgatggacttggag ggcaagcagggcaacttcaagaacctgagggagtttgtgttcaagaacattgatggctacttcaagatttacagcaaacaca caccaatcaacctggtgagggacctgccacagggcttctctgccttggaaccactggtgacctgccaattggcatcaaca tcaccaggttccagaccctgctggctctgcacaggtcctacctgacacctggagactcctcctctggctggacagcaggag cagcagcctactatgtgggctacctccaaccaaggaccttcctgctgaaatacaatgagaatggcaccatcacagatgctgt ggactgtgccctggacccactgtctgagaccaagtgtaccctgaaatccttcacagtggagaagggcatctaccagacca gcaacttcagggtccaaccaacagagagcattgtgaggtttccaaacatcaccaacctgtgtccatttggagaggtgttcaat gccaccaggtttgcctctgtctatgcctggaacaggaagaggattagcaactgtgtggctgactactctgtgctctacaactc tgcctccttcagcaccttcaagtgttatggagtgagcccaaccaaactgaatgacctgtgtttcaccaatgtctatgctgactc ctttgtgattaggggagatgaggtgagacagattgcccctggacaaacaggcaagattgctgactacaactacaaactgcc tgatgacttcacaggctgtgtgattgcctggaacagcaacaacctggacagcaaggtggggcaactacaactacctcta cagactgacaggaagagcaacctgaaaccatttgagagggacatcagcacagagatttaccaggctggcagcacaccat gtaatggagtggagggcttcaactgttactaccactccaatcctatggatccaaccaaccaatggagtgggctaccaacca tacagggtggtggtgctgtcattgaactgctccatgcccctgccacagtgtgtggaccaaagaagagcaccaacctggtg aagaacaagtgtgtgaacttcaacttcaatggactgacaggcacaggagtgctgacagagagcaacaagaagacctgcc attccaacagtaggcagggacattgctgacaccacagatgctgtgagggacccacagaccaggagattctggacatcac accatgacctaggaggagtgtctgtgattacacctggcaccaacaccagcaaccaggtggctgtgctctaccaggatgtg aactgtactgaggtgcctgtggctatccatgctgaccaacttacaccaacctggagggtctacagcacaggcagcaatgtgt tccagaccagggctggctgtctgattggagcagagcatgtgaacaactcctatgagtgtgacatcccaattggagcaggca tctgtgcctcctaccagacccagaccaacagcccaaggagggcaaggtctgtggcaagcagagcatcattgcctacaca atgagtctgggagcagagaactctgtggcttacagcaacaacagcattgccatcccaaccaacttcaccatctctgtgacca cagagattctgcctgtgagtatgaccaagacctctgtggactgtacaatgtatatctgtggagacagcacagagtgtagcaa cctgctgctccaatatggctccactgtacccaacttaacagggctctgacaggcattgctgtggaacaggacaagaacacc caggaggtgatgcccaggtgaagcagatttacaagacacctccaatcaaggactaggaggcttcaacttcagccagattc tgcctgacccaagcaagccaagcaagaggtcatcattgaggacctgctgacaacaaggtgaccctggctgatgctggct tcatcaagcaatatggagactgtctgggagacattgctgccagggacctgatagtgcccagaagttcaatggactgacagt gctgcctccactgctgacagatgagatgattgcccaatacacctctgccctgctggctggcaccatcacctctggctggacc taggagcaggagcagccctccaaatcccatttgctatgcagatggcttacaggacaatggcattggagtgacccagaatgt gctctatgagaaccagaaactgattgccaaccagttcaactctgccattggcaagattcaggactccctgtccagcacagcc tctgccctgggcaaactccaagatgtggtgaaccagaatgcccaggctctgaacaccctggtgaagcaactaccagcaac taggagccatctcctctgtgctgaatgacatcctgagcagactggacaaggtggaggctgaggtccagattgacagactg attacaggcagactccaatccctccaaacctatgtgacccaacaacttatcagggctgctgagattagggcatctgccaacc tggctgccaccaagatgagtgagtgtgtgctgggacaaagcaagagggtggacactgtggcaagggctaccacctgatg agattccacagtctgcccctcatggagtggtgacctgcatgtgacctatgtgcctgcccaggagaagaacttccaccacagc ccctgccatctgccatgatggcaaggctcactaccaagggagggagtgatgtgagcaatggcacccactggtagtgacc cagaggaacactatgaaccacagattatcaccacagacaacacctagtgtctggcaactgtgatgtggtgattggcattgtg aacaacacagtctatgacccactccaacctgaactggactcatcaaggaggaactggacaaatacttcaagaaccacacc
```

-continued agccctgatgtggacctgggagacatctctggcatcaatgcctctgtggtgaacatccagaaggagattgacagactgaat gaggtggctaagaacctgaatgagtccctgattgacctccaagaactgggcaaatatgaacaatacatcaagtggccacat catcaccaccatcactaa 6. S-ECD (AA Val16-Gln1208 (SEQ ID NO: 16)) Protein sequence
VNLTTRTQLPPAYTNSFTRGVYYPDKVFRSSVLHSTQDLFLPFFSNVTWFHAIH

VSGTNGTKRFDNPVLPFNDGVYFASTEKSNIIRGWIFGTTLDSKTQSLLIVNNA

TNVVIKVCEFQFCNDPFLGVYYHKNNKSWMESEFRVYSSANNCTFEYVSQPF

LMDLEGKQGNFKNLREFVFKNIDGYFKIYSKHTPINLVRDLPQGFSALEPLVD

LPIGINITRFQTLLALHRSYLTPGDSSSGWTAGAAAYYVGYLQPRTFLLKYNEN

GTITDAVDCALDPLSETKCTLKSFTVEKGIYQTSNFRVQPTESIVRFPNITNLCP

FGEVFNATRFASVYAWNRKRISNCVADYSVLYNSASFSTFKCYGVSPTKLNDL

CFTNVYADSFVIRGDEVRQIAPGQTGKIADYNYKLPDDFTGCVIAWNSNNLDS

KVGGNYNYLYRLFRKSNLKPFERDISTEIYQAGSTPCNGVEGFNCYFPLQSYG

FQPTNGVGYQPYRVVVLSFELLHAPATVCGPKKSTNLVKNKCVNFNFNGLTG

TGVLTESNKKFLPFQQFGRDIADTTDAVRDPQTLEILDITPCSFGGVSVITPGTN

TSNQVAVLYQDVNCTEVPVAIHADQLTPTWRVYSTGSNVFQTRAGCLIGAEH

VNNSYECDIPIGAGICASYQTQTNSPRRARSVASQSIIAYTMSLGAENSVAYSN

NSIAIPTNFTISVTTEILPVSMTKTSVDCTMYICGDSTECSNLLLQYGSFCTQLN

RALTGIAVEQDKNTQEVFAQVKQIYKTPPIKDFGGFNFSQILPDPSKPSKRSFIE

DLLFNKVTLADAGFIKQYGDCLGDIAARDLICAQKFNGLTVLPPLLTDEMIAQ

YTSALLAGTITSGWTFGAGAALQIPFAMQMAYRFNGIGVTQNVLYENQKLIA

NQFNSAIGKIQDSLSSTASALGKLQDVVNQNAQALNTLVKQLSSNFGAISSVL

NDILSRLDKVEAEVQIDRLITGRLQSLQTYVTQQLIRAAEIRASANLAATKMSE

CVLGQSKRVDFCGKGYHLMSFPQSAPHGVVFLHVTYVPAQEKNFTTAPAICH

DGKAHFPREGVFVSNGTHWFVTQRNFYEPQIITTDNTFVSGNCDVVIGIVNNT

VYDPLQPELDSFKEELDKYFKNHTSPDVDLGDISGINASVVNIQKEIDRLNEVA

KNLNESLIDLQELGKYEQHHHHHH

6. S-ECD cloning sequence
S-ECD (AA Met1 -Gln1208 (SEQ ID NO: 17)) which was subcloned into pcDNA
vector by 5'XbaI/3'AgeI; includes the optimized DNA codon; with the underlined
signal peptide coding section (Accession #YP_009724390.1)
<u>atgtttgttcctggtgctgctgccactggtgtccagccagtgt</u>gtgaacctgaccaccaggacccaacttcctcctgcctac accaactccttcaccaggggagtctactaccctgacaaggtgttcaggtcctctgtgctgcacagcacccaggacctgttcc tgccattcttcagcaatgtgacctggttccatgccatccatgtgtctggcaccaatggcaccaagagggtttgacaacctgtg ctgccattcaatgatggagtctactttgccagcacagagaagagcaacatcatcaggggctggattttggcaccaccctgg acagcaagacccagtccctgctgattgtgaacaatgccaccaatgtggtgattaaggtgtgtgagttccagttctgtaatgac ccattcctgggagtctactaccacaagaacaacaagtcctggatggagtctgagttcagggtctactcctctgccaacaact gtacctttgaatatgtgagccaaccattcctgatggacttggagggcaagcagggcaacttcaagaacctgagggagtttgt gttcaagaacattgatggctacttcaagatttacagcaaacacacaccaatcaacctggtgagggacctgccacagggcttc tctgcccttgaaccactggtggacctgccaattggcatcaacatcaccaggttccagaccctgctggctctgcacaggtcct acctgacacctggagactcctcctctggctggacagcaggagcagcagcctactatgtgggctacctccaaccaaggacc ttcctgctgaaatacaatgagaatggcaccatcacagatgctgtggactgtgccctggacccactgtctgagaccaagtgta ccctgaaatccttcacagtggagaagggcatctaccagaccagcaacttcagggtccaaccaacagagagcattgtgagg -continued

```
tttccaaacatcaccaacctgtgtccatttggagaggtgttcaatgccaccaggtttgcctctgtctatgcctggaacaggaag aggattagcaactgtgtggctgactactctgtgctctacaactctgcctccttcagcaccttcaagtgttatggagtgagccca accaaactgaatgacctgtgtttcaccaatgtctatgctgactcattgtgattaggggagatgaggtgagacagattgcccct ggacaaacaggcaagattgctgactacaactacaaactgcctgatgacttcacaggctgtgtgattgcctggaacagcaac aacctggacagcaaggtgggaggcaactacaactacctctacagactgttcaggaagagcaacctgaaaccatttgagag ggacatcagcacagagatttaccaggctggcagcacaccatgtaatggagtggagggcttcaactgttactccactccaa tcctatggcttccaaccaaccaatggagtgggctaccaaccatacagggtggtggtgctgtcctttgaactgctccatgccc ctgccacagtgtgtggaccaaagaagagcaccaacctggtgaagaacaagtgtgtgaacttcaacttcaatggactgaca ggcacaggagtgctgacagagagcaacaagaagttcctgccattccaacagtttggcagggacattgctgacaccacaga tgctgtgagggaccccacagaccttggagattctggacatcacaccatgttcctttggaggagtgtctgtgattacacctggca ccaacaccagcaaccaggtggctgtgctctaccaggatgtgaactgtactgaggtgcctgtggctatccatgctgaccaact tacaccaacctggagggtctacagcacaggcagcaatgtgttccagaccagggctggctgtctgattggagcagagcatg tgaacaactcctatgagtgtgacatcccaattggagcaggcatctgtgcctcctaccagacccagaccaacagcccaagga gggcaaggtctgtggcaagccagagcatcattgcctacacaatgagtctgggagcagagaactctgtggcttacagcaac aacagcattgccatcccaaccaacttcaccatctctgtgaccacagagattctgcctgtgagtatgaccaagacctctgtgga ctgtacaatgtatatctgtggagacagcacagagtgtagcaacctgctgctccaatatggctccttctgtacccaacttaacag ggctctgacaggcattgctgtggaacaggacaagaacacccaggaggtgtttgcccaggtgaagcagatttacaagacac ctccaatcaaggactttggaggcttcaacttcagccagattctgcctgacccaagcaagccaagcaagaggtccttcattga ggacctgctgttcaacaaggtgacccctggctgatgctggcttcatcaagcaatatggagactgtctgggagacattgctgcc agggacctgatttgtgcccagaagttcaatggactgacagtgctgcctccactgctgacagatgagatgattgcccaataca cctctgccctgctggctggcaccatcacctctggctggacctttggagcaggagcagccctccaaatcccatttgctatgca gatggcttacaggttcaatggcattggagtgacccagaatgtgctctatgagaaccagaaactgattgccaaccagttcaac tctgccattggcaagattcaggactccctgtccagcacagcctctgccctgggcaaactccaagatgtggtgaaccagaat gcccaggctctgaacaccctggtgaagcaactttccagcaactttggagccatctcctctgtgctgaatgacatcctgagca gactggacaaggtggaggctgaggtccagattgacagactgattacaggcagactccaatccctccaaacctatgtgacc caacaacttatcagggctgctgagattagggcatctgccaacctggctgccaccaagatgagtgagtgtgtgctgggacaa agcaagagggtggacttctgtggcaagggctaccacctgatgagttttccacagtctgcccctcatggagtggtgttcctgc atgtgacctatgtgcctgcccaggagaagaacttcaccacagcccctgccatctgccatgatggcaaggctcactttccaag ggagggagtgtttgtgagcaatggcacccactggtttgtgacccagaggaacttctatgaaccacagattatcaccacaga caacaccttgtgtctgcaactgtgatgtggtgattggcattgtgaacaacacagtctatgacccactccaacctgaactgg actccttcaaggaggaactggacaaatacttcaagaaccacaccagccctgatgtggacctgggagacatctctggcatca atgcctctgtggtgaacatccagaaggagattgacagactgaatgaggtggctaagaacctgaatgagtccctgattgacct ccaagaactgggcaaatatgaacaatacatcaagtggccacatcatcaccaccatcactaa
```

Protein sequence (AA Met1-Gln1208(SEQ ID NO: 18)), with signal peptide underlined <u>MFVFLVLLPLVSSQC</u>VNLTTRTQLPPAYTNSFTRGVYYPDKVFRSSVLHSTQDL

FLPFFSNVTWFHAIHVSGTNGTKRFDNPVLPFNDGVYFASTEKSNIIRGWIFGT

TLDSKTQSLLIVNNATNVVIKVCEFQFCNDPFLGVYYHKNNKSWMESEFRVY

SSANNCTFEYVSQPFLMDLEGKQGNFKNLREFVFKNIDGYFKIYSKHTPINLV

RDLPQGFSALEPLVDLPIGINITRFQTLLALHRSYLTPGDSSSGWTAGAAAYYV

GYLQPRTFLLKYNENGTITDAVDCALDPLSETKCTLKSFTVEKGIYQTSNFRV

QPTESIVRFPNITNLCPFGEVFNATRFASVYAWNRKRISNCVADYSVLYNSASFS

-continued

TFKCYGVSPTKLNDLCFTNVYADSFVIRGDEVRQIAPGQTGKIADYNYKLPDD

FTGCVIAWNSNNLDSKVGGNYNYLYRLFRKSNLKPFERDISTEIYQAGSTPCN

GVEGFNCYFPLQSYGFQPTNGVGYQPYRVVVLSFELLHAPATVCGPKKSTNL

VKNKCVNFNFNGLTGTGVLTESNKKFLPFQQFGRDIADTTDAVRDPQTLEILDI

TPCSFGGVSVITPGTNTSNQVAVLYQDVNCTEVPVAIHADQLTPTWRVYSTGS

NVFQTRAGCLIGAEHVNNSYECDIPIGAGICASYQTQTNSPRRARSVASQSIIA

YTMSLGAENSVAYSNNSIAIPTNFTISVTTEILPVSMTKTSVDCTMYICGDSTEC

SNLLLQYGSFCTQLNRALTGIAVEQDKNTQEVFAQVKQIYKTPPIKDFGGFNFS

QILPDPSKPSKRSFIEDLLFNKVTLADAGFIKQYGDCLGDIAARDLICAQKFNG

LTVLPPLLTDEMIAQYTSALLAGTITSGWTFGAGAALQIPFAMQMAYRFNGIG

VTQNVLYENQKLIANQFNSAIGKIQDSLSSTASALGKLQDVVNQNAQALNTL

VKQLSSNFGAISSVLNDILSRLDKVEAEVQIDRLITGRLQSLQTYVTQQLIRAA

EIRASANLAATKMSECVLGQSKRVDFCGKGYHLMSFPQSAPHGVVFLHVTYV

PAQEKNFTTAPAICHDGKAHFPREGVFVSNGTHWFVTQRNFYEPQIITTDNTF

VSGNCDVVIGIVNNTVYDPLQPELDSFKEELDKYFKNHTSPDVDLGDISGINA

SVVNIQKEIDRLNEVAKNLNESLIDLQELGKYEQHHHHHH

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES

1. Coutard B, Valle C, de Lamballerie X, Canard B, Seidah N G, Decroly E. The spike glycoprotein of the new coronavirus 2019-nCoV contains a furin-like cleavage site absent in CoV of the same Clade. Antiviral Res. 2020; 176:104742. doi:10.1016/j.antiviral.2020.104742
2. Hoffmann M, Kleine-Weber H, Schroeder S, et al. SARS-CoV-2 Cell Entry Depends on ACE2 and TMPRSS2 and Is Blocked by a Clinically Proven Protease Inhibitor. Cell. 2020; 181(2):271-280.e8. doi:10.1016/j.cell.2020.02.052
3. Furin See Wikipedia Website
4. Stadlbauer D, Amanat F, Chromikova V, et al. SARS-CoV-2 Seroconversion in Humans: A Detailed Protocol for a Serological Assay, Antigen Production, and Test Setup. Curr Protoc Microbiol. 2020; 57(1):e100. doi: 10.1002/cpmc.100

What is claimed is:

1. A method of generating the mature, active form of a SARS-CoV-2 S protein, comprising:

generating host cells which lack the ability to express furin but which express SARS-CoV-2 spike protein using a CRISPR Cas9 transfection protocol having sgRNA scaffolds: GATGCGCACAGCCCACGTGT (SEQ ID NO:19); and ACAGTGTGGCACGGAAGCAT (SEQ ID NO:20);

expressing the SARS-CoV-2 spike protein in said host cells; and cleaving the SARS-CoV-2 spike protein with furin at a cleavage site between amino acid Arginine 670 and amino acid Serine 671 in the extracellular domain shown in SEQ ID NO.: 16, to yield the mature, active form of SARS Cov2 S protein containing the 51 and S2 subunits.

* * * * *

SEQUENCE LISTING

<160> NUMBER OF SEQ ID NOS: 20

<210> SEQ ID NO 1
<211> LENGTH: 91

<212> TYPE: DNA
<213> ORGANISM: Homo sapiens

<400> SEQUENCE: 1
gaaggtcttc accaacacgt gggctgtgcg catccctgga ggcccagcgg tggccaacag    60
tgtggcacgg aagcatgggt tcctcaacct g    91

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gaaggtcttc accaacacat gggttcctca acctg    35

<210> SEQ ID NO 3
<211> LENGTH: 56
<212> TYPE: DNA
<213> ORGANISM: Homo sapiens

<400> SEQUENCE: 3
gtgggctgtg cgcatccctg gaggcccagc ggtggccaac agtgtggcac ggaagc    56

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 4

His His His His His His
1               5

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
caccgatgcg cacagcccac gtgt    24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aaacacacgt gggctgtgcg catc    24

<210> SEQ ID NO 7
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 7
caccacagtg tggcacggaa gcat                                              24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aaacatgctt ccgtgccaca ctgt                                              24

<210> SEQ ID NO 9
<211> LENGTH: 468
<212> TYPE: DNA
<213> ORGANISM: Homo sapiens

<400> SEQUENCE: 9
cctgcccgtc tcggccccat gcccccacca gtcagcccca ggccacaggc agtgagcagg        60
cacctgggag ccgaggccct gtgaccaggc caaggagacg ggcgctccag ggtcccagcc       120
acctgtcccc cccatggagc tgaggccctg gttgctatgg gtggtagcag caacaggaac       180
cttggtcctg ctagcagctg atgctcaggg ccagaaggtc ttcaccaaca cgtgggctgt       240
gcgcatccct ggaggcccag cggtggccaa cagtgtggca cggaagcatg ggttcctcaa       300
cctgggccag gtaggtgttc ccccacagga cactgccagg gggtgggacc agagaagaca       360
gggattctgg gagcaggagc tgttggcctt gtttgctcag gggcatctgg gtagccggca       420
tgttctgggt ggccatgagc aaagcacagg tggttcaggc aagcagca                    468

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcctctcagg gtcggcactc                                                   20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gctgcttgcc tgaaccacct                                                   20

<210> SEQ ID NO 12
<211> LENGTH: 406
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 12

```
cgtctcggcc ccatgccccc accagtcagc cccgggccac aggcagtgag caggcacctg      60
ggagccgagg ccctgtgacc aggccaagga gacgggcgct ccagggtccc agccacctgt     120
cccccccatg gagctgaggc cctggttgct atgggtggta gcagcaacag gaaccttggt     180
cctgctagca gctgatgctc agggccagaa ggtcttcacc aacacatggg ttcctcaacc     240
tgggccaggt aggtgttccc ccacaggaca ctgccagggg gtgggaccag agaagacagg     300
gattctggga gcaggagctg ttggccttgt tgctcaggg catctgggt agccggcatg       360
ttctgggtgg ccatgagcaa agcacaggtg gttcaggcaa gcagca                    406
```

<210> SEQ ID NO 13
<211> LENGTH: 794
<212> TYPE: PRT
<213> ORGANISM: Homo sapiens

<400> SEQUENCE: 13

```
Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
            20                  25                  30

Thr Trp Ala Val Arg Ile Pro Gly Gly Pro Ala Val Ala Asn Ser Val
        35                  40                  45

Ala Arg Lys His Gly Phe Leu Asn Leu Gly Gln Ile Phe Gly Asp Tyr
    50                  55                  60

Tyr His Phe Trp His Arg Gly Val Thr Lys Arg Ser Leu Ser Pro His
65                  70                  75                  80

Arg Pro Arg His Ser Arg Leu Gln Arg Glu Pro Gln Val Gln Trp Leu
                85                  90                  95

Glu Gln Gln Val Ala Lys Arg Arg Thr Lys Arg Asp Val Tyr Gln Glu
            100                 105                 110

Pro Thr Asp Pro Lys Phe Pro Gln Gln Trp Tyr Leu Ser Gly Val Thr
        115                 120                 125

Gln Arg Asp Leu Asn Val Lys Ala Ala Trp Ala Gln Gly Tyr Thr Gly
    130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
            180                 185                 190

Arg His Gly Thr Arg Cys Ala Gly Glu Val Ala Ala Val Ala Asn Asn
        195                 200                 205

Gly Val Cys Gly Val Gly Val Ala Tyr Asn Ala Arg Ile Gly Gly Val
    210                 215                 220

Arg Met Leu Asp Gly Glu Val Thr Asp Ala Val Glu Ala Arg Ser Leu
225                 230                 235                 240

Gly Leu Asn Pro Asn His Ile His Ile Tyr Ser Ala Ser Trp Gly Pro
                245                 250                 255

Glu Asp Asp Gly Lys Thr Val Asp Gly Pro Ala Arg Leu Ala Glu Glu
            260                 265                 270

Ala Phe Phe Arg Gly Val Ser Gln Gly Arg Gly Gly Leu Gly Ser Ile
        275                 280                 285
```

-continued

```
Phe Val Trp Ala Ser Gly Asn Gly Gly Arg Glu His Asp Ser Cys Asn
290                 295                 300
Cys Asp Gly Tyr Thr Asn Ser Ile Tyr Thr Leu Ser Ile Ser Ser Ala
305                 310                 315                 320
Thr Gln Phe Gly Asn Val Pro Trp Tyr Ser Glu Ala Cys Ser Ser Thr
            325                 330                 335
Leu Ala Thr Thr Tyr Ser Ser Gly Asn Gln Asn Glu Lys Gln Ile Val
            340                 345                 350
Thr Thr Asp Leu Arg Gln Lys Cys Thr Glu Ser His Thr Gly Thr Ser
        355                 360                 365
Ala Ser Ala Pro Leu Ala Ala Gly Ile Ile Ala Leu Thr Leu Glu Ala
370                 375                 380
Asn Lys Asn Leu Thr Trp Arg Asp Met Gln His Leu Val Val Gln Thr
385                 390                 395                 400
Ser Lys Pro Ala His Leu Asn Ala Asn Asp Trp Ala Thr Asn Gly Val
            405                 410                 415
Gly Arg Lys Val Ser His Ser Tyr Gly Tyr Gly Leu Leu Asp Ala Gly
            420                 425                 430
Ala Met Val Ala Leu Ala Gln Asn Trp Thr Thr Val Ala Pro Gln Arg
        435                 440                 445
Lys Cys Ile Ile Asp Ile Leu Thr Glu Pro Lys Asp Ile Gly Lys Arg
450                 455                 460
Leu Glu Val Arg Lys Thr Val Thr Ala Cys Leu Gly Glu Pro Asn His
465                 470                 475                 480
Ile Thr Arg Leu Glu His Ala Gln Ala Arg Leu Thr Leu Ser Tyr Asn
            485                 490                 495
Arg Arg Gly Asp Leu Ala Ile His Leu Val Ser Pro Met Gly Thr Arg
            500                 505                 510
Ser Thr Leu Leu Ala Ala Arg Pro His Asp Tyr Ser Ala Asp Gly Phe
        515                 520                 525
Asn Asp Trp Ala Phe Met Thr Thr His Ser Trp Asp Glu Asp Pro Ser
530                 535                 540
Gly Glu Trp Val Leu Glu Ile Glu Asn Thr Ser Glu Ala Asn Asn Tyr
545                 550                 555                 560
Gly Thr Leu Thr Lys Phe Thr Leu Val Leu Tyr Gly Thr Ala Pro Glu
            565                 570                 575
Gly Leu Pro Val Pro Pro Glu Ser Ser Gly Cys Lys Thr Leu Thr Ser
            580                 585                 590
Ser Gln Ala Cys Val Val Cys Glu Glu Gly Phe Ser Leu His Gln Lys
        595                 600                 605
Ser Cys Val Gln His Cys Pro Pro Gly Phe Ala Pro Gln Val Leu Asp
610                 615                 620
Thr His Tyr Ser Thr Glu Asn Asp Val Glu Thr Ile Arg Ala Ser Val
625                 630                 635                 640
Cys Ala Pro Cys His Ala Ser Cys Ala Thr Cys Gln Gly Pro Ala Leu
            645                 650                 655
Thr Asp Cys Leu Ser Cys Pro Ser His Ala Ser Leu Asp Pro Val Glu
            660                 665                 670
Gln Thr Cys Ser Arg Gln Ser Gln Ser Ser Arg Glu Ser Pro Pro Gln
        675                 680                 685
Gln Gln Pro Pro Arg Leu Pro Pro Glu Val Glu Ala Gly Gln Arg Leu
690                 695                 700
Arg Ala Gly Leu Leu Pro Ser His Leu Pro Glu Val Val Ala Gly Leu
```

```
                705                 710                 715                 720
Ser Cys Ala Phe Ile Val Leu Val Phe Val Thr Val Phe Leu Val Leu
                    725                 730                 735

Gln Leu Arg Ser Gly Phe Ser Phe Arg Gly Val Lys Val Tyr Thr Met
            740                 745                 750

Asp Arg Gly Leu Ile Ser Tyr Lys Gly Leu Pro Pro Glu Ala Trp Gln
        755                 760                 765

Glu Glu Cys Pro Ser Asp Ser Glu Glu Asp Gly Arg Gly Glu Arg
    770                 775                 780

Thr Ala Phe Ile Lys Asp Gln Ser Ala Leu
785                 790

<210> SEQ ID NO 14
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
            20                  25                  30

Thr Trp

<210> SEQ ID NO 15
<211> LENGTH: 3615
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gtgaacctga ccaccaggac ccaacttcct cctgcctaca ccaactcctt caccaggggga    60 gtctactacc ctgacaaggt gttcaggtcc tctgtgctgc acagcaccca ggacctgttc   120
ctgccattct tcagcaatgt gacctggttc catgccatcc atgtgtctgg caccaatggc   180
accaagaggt ttgacaaccc tgtgctgcca ttcaatgatg agtctactt tgccagcaca   240 gagaagagca acatcatcag gggctggatt tttggcacca ccctggacag caagacccag   300
tccctgctga ttgtgaacaa tgccaccaat gtggtgatta ggtgtgtga gttccagttc   360 tgtaatgacc cattcctggg agtctactac acaagaaca acaagtcctg gatggagtct   420
gagttcaggg tctactcctc tgccaacaac tgtaccttttg aatatgtgag ccaaccattc   480
ctgatggact ggagggcaa gcagggcaac ttcaagaacc tgagggagtt tgtgttcaag   540
aacattgatg ctacttcaa gatttacagc aaacacacac caatcaacct ggtgagggac   600
ctgccacagg gcttctctgc cttggaacca ctggtggacc tgccaattgg catcaacatc   660
accaggttcc agaccctgct ggctctgcac aggtcctacc tgacacctgg agactcctcc   720
tctggctgga cagcaggagc agcagcctac tatgtgggct acctccaacc aaggaccttc   780
ctgctgaaat acaatgagaa tggcaccatc acagatgctg tggactgtgc cctggaccca   840
ctgtctgaga ccagtgtgta cctgaaatcc ttcacagtgg agaagggcat ctaccagacc   900
agcaacttca gggtccaacc aacagagagc attgtgaggt ttccaaacat caccaacctg   960
```

```
tgtccatttg agaggtgtt caatgccacc aggtttgcct ctgtctatgc ctggaacagg      1020
aagaggatta gcaactgtgt ggctgactac tctgtgctct acaactctgc ctccttcagc    1080
accttcaagt gttatggagt gagcccaacc aaactgaatg acctgtgttt caccaatgtc    1140
tatgctgact cctttgtgat taggggagat gaggtgagac agattgcccc tggacaaaca    1200
ggcaagattg ctgactacaa ctacaaactg cctgatgact tcacaggctg tgtgattgcc    1260
tggaacagca caacctgga cagcaaggtg ggaggcaact acaactacct ctacagactg     1320
ttcaggaaga gcaacctgaa accatttgag agggacatca gcacagagat ttaccaggct    1380
ggcagcacac catgtaatgg agtggagggc ttcaactgtt actttccact ccaatcctat    1440
ggcttccaac aaccaatgg agtgggctac caaccataca gggtggtggt gctgtccttt      1500
gaactgctcc atgcccctgc cacagtgtgt ggaccaaaga gagcaccaa cctggtgaag      1560 aacaagtgtg tgaacttcaa cttcaatgga ctgacaggca caggagtgct gacagagagc    1620
aacaagaagt tcctgccatt ccaacagttt ggcagggaca ttgctgacac cacagatgct    1680
gtgagggacc cacagacctt ggagattctg acatcacac catgttcctt tggaggagtg      1740
tctgtgatta cacctggcac caacaccagc aaccaggtgg ctgtgctcta ccaggatgtg    1800
aactgtactg aggtgcctgt ggctatccat gctgaccaac ttacaccaac ctggagggtc    1860
tacagcacag gcagcaatgt gttccagacc agggctggct gtctgattgg agcagagcat    1920
gtgaacaact cctatgagtg tgacatccca attggagcag gcatctgtgc ctcctaccag    1980
acccagacca acagcccaag gagggcaagg tctgtggcaa gccagagcat cattgcctac    2040
acaatgagtc tgggagcaga gaactctgtg gcttacagca acaacagcat tgccatccca    2100
accaacttca ccatctctgt gaccacagag attctgcctg tgagtatgac caagacctct    2160
gtggactgta caatgtatat ctgtggagac agcacagagt gtagcaacct gctgctccaa    2220
tatggctcct tctgtaccca acttaacagg gctctgacag gcattgctgt ggaacaggac    2280
aagaacaccc aggaggtgtt tgcccaggtg aagcagattt acaagacacc tccaatcaag    2340
gactttggag gcttcaactt cagccagatt ctgcctgacc caagcaagcc aagcaagagg    2400
tccttcattg aggacctgct gttcaacaag gtgaccctgg ctgatgctgg cttcatcaag    2460
caatatggag actgtctggg agacattgct gccagggacc tgatttgtgc ccagaagttc    2520
aatggactga cagtgctgcc tccactgctg acagatgaga tgattgccca atacacctct    2580
gccctgctgg ctggcaccat cacctctggc tggaccttg gagcaggagc agccctccaa    2640
atcccatttg ctatgcagat ggcttacagg ttcaatggca ttggagtgac ccagaatgtg    2700
ctctatgaga accagaaact gattgccaac cagttcaact ctgccattgg caagattcag    2760
gactccctgt ccagcacagc ctctgccctg ggcaaactcc aagatgtggt gaaccagaat    2820
gcccaggctc tgaacaccct ggtgaagcaa cttttccagca actttggagc catctcctct    2880
gtgctgaatg acatcctgag cagactggac aaggtggagg ctgaggtcca gattgacaga    2940
ctgattacag gcagactcca atccctccaa acctatgtga cccaacaact tatcagggct    3000
gctgagatta gggcatctgc caacctggct gccaccaaga tgagtgagtg tgtgctggga    3060
caaagcaaga gggtggactt ctgtggcaag ggctaccacc tgatgagttt ccacagtct     3120 gcccctcatg gagtggtgtt cctgcatgtg acctatgtgc ctgcccagga agaacttc      3180 accacagccc ctgccatctg ccatgatggc aaggctcact ttccaaggga gggagtgttt    3240
gtgagcaatg gcacccactg gtttgtgacc cagaggaact tctatgaacc acagattatc    3300
accacagaca acacctttgt gtctggcaac tgtgatgtgg tgattggcat tgtgaacaac    3360
```

```
acagtctatg acccactcca acctgaactg gactccttca aggaggaact ggacaaatac    3420
ttcaagaacc acaccagccc tgatgtggac ctgggagaca tctctggcat caatgcctct    3480
gtggtgaaca tccagaagga gattgacaga ctgaatgagg tggctaagaa cctgaatgag    3540
tccctgattg acctccaaga actgggcaaa tatgaacaat acatcaagtg gccacatcat    3600
caccaccatc actaa                                                    3615
```

<210> SEQ ID NO 16
<211> LENGTH: 1199
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Val Asn Leu Thr Thr Arg Thr Gln Leu Pro Pro Ala Tyr Thr Asn Ser
1               5                   10                  15

Phe Thr Arg Gly Val Tyr Tyr Pro Asp Lys Val Phe Arg Ser Ser Val
            20                  25                  30

Leu His Ser Thr Gln Asp Leu Phe Leu Pro Phe Phe Ser Asn Val Thr
        35                  40                  45

Trp Phe His Ala Ile His Val Ser Gly Thr Asn Gly Thr Lys Arg Phe
    50                  55                  60

Asp Asn Pro Val Leu Pro Phe Asn Asp Gly Val Tyr Phe Ala Ser Thr
65                  70                  75                  80

Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
            100                 105                 110

Ile Lys Val Cys Glu Phe Gln Phe Cys Asn Asp Pro Phe Leu Gly Val
        115                 120                 125

Tyr Tyr His Lys Asn Asn Lys Ser Trp Met Glu Ser Glu Phe Arg Val
    130                 135                 140

Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
                165                 170                 175

Phe Val Phe Lys Asn Ile Asp Gly Tyr Phe Lys Ile Tyr Ser Lys His
            180                 185                 190

Thr Pro Ile Asn Leu Val Arg Asp Leu Pro Gln Gly Phe Ser Ala Leu
        195                 200                 205

Glu Pro Leu Val Asp Leu Pro Ile Gly Ile Asn Ile Thr Arg Phe Gln
    210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Ala Tyr Tyr Val Gly Tyr Leu Gln
                245                 250                 255

Pro Arg Thr Phe Leu Leu Lys Tyr Asn Glu Asn Gly Thr Ile Thr Asp
            260                 265                 270

Ala Val Asp Cys Ala Leu Asp Pro Leu Ser Glu Thr Lys Cys Thr Leu
        275                 280                 285

Lys Ser Phe Thr Val Glu Lys Gly Ile Tyr Gln Thr Ser Asn Phe Arg
    290                 295                 300
```

```
Val Gln Pro Thr Glu Ser Ile Val Arg Phe Pro Asn Ile Thr Asn Leu
305                 310                 315                 320

Cys Pro Phe Gly Glu Val Phe Asn Ala Thr Arg Phe Ala Ser Val Tyr
            325                 330                 335

Ala Trp Asn Arg Lys Arg Ile Ser Asn Cys Val Ala Asp Tyr Ser Val
            340                 345                 350

Leu Tyr Asn Ser Ala Ser Phe Ser Thr Phe Lys Cys Tyr Gly Val Ser
            355                 360                 365

Pro Thr Lys Leu Asn Asp Leu Cys Phe Thr Asn Val Tyr Ala Asp Ser
370                 375                 380

Phe Val Ile Arg Gly Asp Glu Val Arg Gln Ile Ala Pro Gly Gln Thr
385                 390                 395                 400

Gly Lys Ile Ala Asp Tyr Asn Tyr Lys Leu Pro Asp Asp Phe Thr Gly
            405                 410                 415

Cys Val Ile Ala Trp Asn Ser Asn Asn Leu Asp Ser Lys Val Gly Gly
            420                 425                 430

Asn Tyr Asn Tyr Leu Tyr Arg Leu Phe Arg Lys Ser Asn Leu Lys Pro
            435                 440                 445

Phe Glu Arg Asp Ile Ser Thr Glu Ile Tyr Gln Ala Gly Ser Thr Pro
450                 455                 460

Cys Asn Gly Val Glu Gly Phe Asn Cys Tyr Phe Pro Leu Gln Ser Tyr
465                 470                 475                 480

Gly Phe Gln Pro Thr Asn Gly Val Gly Tyr Gln Pro Tyr Arg Val Val
            485                 490                 495

Val Leu Ser Phe Glu Leu Leu His Ala Pro Ala Thr Val Cys Gly Pro
            500                 505                 510

Lys Lys Ser Thr Asn Leu Val Lys Asn Lys Cys Val Asn Phe Asn Phe
            515                 520                 525

Asn Gly Leu Thr Gly Thr Gly Val Leu Thr Glu Ser Asn Lys Lys Phe
            530                 535                 540

Leu Pro Phe Gln Gln Phe Gly Arg Asp Ile Ala Asp Thr Thr Asp Ala
545                 550                 555                 560

Val Arg Asp Pro Gln Thr Leu Glu Ile Leu Asp Ile Thr Pro Cys Ser
            565                 570                 575

Phe Gly Gly Val Ser Val Ile Thr Pro Gly Thr Asn Thr Ser Asn Gln
            580                 585                 590

Val Ala Val Leu Tyr Gln Asp Val Asn Cys Thr Glu Val Pro Val Ala
            595                 600                 605

Ile His Ala Asp Gln Leu Thr Pro Thr Trp Arg Val Tyr Ser Thr Gly
610                 615                 620

Ser Asn Val Phe Gln Thr Arg Ala Gly Cys Leu Ile Gly Ala Glu His
625                 630                 635                 640

Val Asn Asn Ser Tyr Glu Cys Asp Ile Pro Ile Gly Ala Gly Ile Cys
            645                 650                 655

Ala Ser Tyr Gln Thr Gln Thr Asn Ser Pro Arg Arg Ala Arg Ser Val
            660                 665                 670

Ala Ser Gln Ser Ile Ile Ala Tyr Thr Met Ser Leu Gly Ala Glu Asn
            675                 680                 685

Ser Val Ala Tyr Ser Asn Asn Ser Ile Ala Ile Pro Thr Asn Phe Thr
            690                 695                 700

Ile Ser Val Thr Thr Glu Ile Leu Pro Val Ser Met Thr Lys Thr Ser
705                 710                 715                 720

Val Asp Cys Thr Met Tyr Ile Cys Gly Asp Ser Thr Glu Cys Ser Asn
```

-continued

```
                725                 730                 735
Leu Leu Leu Gln Tyr Gly Ser Phe Cys Thr Gln Leu Asn Arg Ala Leu
            740                 745                 750

Thr Gly Ile Ala Val Glu Gln Asp Lys Asn Thr Gln Glu Val Phe Ala
            755                 760                 765

Gln Val Lys Gln Ile Tyr Lys Thr Pro Pro Ile Lys Asp Phe Gly Gly
            770                 775                 780

Phe Asn Phe Ser Gln Ile Leu Pro Asp Pro Ser Lys Pro Ser Lys Arg
785                 790                 795                 800

Ser Phe Ile Glu Asp Leu Leu Phe Asn Lys Val Thr Leu Ala Asp Ala
                805                 810                 815

Gly Phe Ile Lys Gln Tyr Gly Asp Cys Leu Gly Asp Ile Ala Ala Arg
                820                 825                 830

Asp Leu Ile Cys Ala Gln Lys Phe Asn Gly Leu Thr Val Leu Pro Pro
                835                 840                 845

Leu Leu Thr Asp Glu Met Ile Ala Gln Tyr Thr Ser Ala Leu Leu Ala
                850                 855                 860

Gly Thr Ile Thr Ser Gly Trp Thr Phe Gly Ala Gly Ala Ala Leu Gln
865                 870                 875                 880

Ile Pro Phe Ala Met Gln Met Ala Tyr Arg Phe Asn Gly Ile Gly Val
                885                 890                 895

Thr Gln Asn Val Leu Tyr Glu Asn Gln Lys Leu Ile Ala Asn Gln Phe
                900                 905                 910

Asn Ser Ala Ile Gly Lys Ile Gln Asp Ser Leu Ser Ser Thr Ala Ser
                915                 920                 925

Ala Leu Gly Lys Leu Gln Asp Val Val Asn Gln Asn Ala Gln Ala Leu
                930                 935                 940

Asn Thr Leu Val Lys Gln Leu Ser Ser Asn Phe Gly Ala Ile Ser Ser
945                 950                 955                 960

Val Leu Asn Asp Ile Leu Ser Arg Leu Asp Lys Val Glu Ala Glu Val
                965                 970                 975

Gln Ile Asp Arg Leu Ile Thr Gly Arg Leu Gln Ser Leu Gln Thr Tyr
                980                 985                 990

Val Thr Gln Gln Leu Ile Arg Ala Ala Glu Ile Arg Ala Ser Ala Asn
                995                 1000                1005

Leu Ala Ala Thr Lys Met Ser Glu Cys Val Leu Gly Gln Ser Lys
                1010                1015                1020

Arg Val Asp Phe Cys Gly Lys Gly Tyr His Leu Met Ser Phe Pro
                1025                1030                1035

Gln Ser Ala Pro His Gly Val Val Phe Leu His Val Thr Tyr Val
                1040                1045                1050

Pro Ala Gln Glu Lys Asn Phe Thr Thr Ala Pro Ala Ile Cys His
                1055                1060                1065

Asp Gly Lys Ala His Phe Pro Arg Glu Gly Val Phe Val Ser Asn
                1070                1075                1080

Gly Thr His Trp Phe Val Thr Gln Arg Asn Phe Tyr Glu Pro Gln
                1085                1090                1095

Ile Ile Thr Thr Asp Asn Thr Phe Val Ser Gly Asn Cys Asp Val
                1100                1105                1110

Val Ile Gly Ile Val Asn Asn Thr Val Tyr Asp Pro Leu Gln Pro
                1115                1120                1125

Glu Leu Asp Ser Phe Lys Glu Glu Leu Asp Lys Tyr Phe Lys Asn
                1130                1135                1140
```

```
His Thr Ser Pro Asp Val Asp Leu Gly Asp Ile Ser Gly Ile Asn
    1145                1150                1155

Ala Ser Val Val Asn Ile Gln Lys Glu Ile Asp Arg Leu Asn Glu
    1160                1165                1170

Val Ala Lys Asn Leu Asn Glu Ser Leu Ile Asp Leu Gln Glu Leu
    1175                1180                1185

Gly Lys Tyr Glu Gln His His  His His His His
    1190                1195

<210> SEQ ID NO 17
<211> LENGTH: 3660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atgtttgtgt tcctggtgct gctgccactg gtgtccagcc agtgtgtgaa cctgaccacc      60
aggacccaac ttcctcctgc ctacaccaac tccttcacca ggggagtcta ctaccctgac     120
aaggtgttca ggtcctctgt gctgcacagc acccaggacc tgttcctgcc attcttcagc     180
aatgtgacct ggttccatgc catccatgtg tctggcacca atggcaccaa gaggtttgac     240
aaccctgtgc tgccattcaa tgatggagtc tactttgcca gcacagagaa gagcaacatc     300
atcaggggct ggatttttgg caccaccctg gacagcaaga cccagtccct gctgattgtg     360
aacaatgcca ccaatgtggt gattaaggtg tgtgagttcc agttctgtaa tgacccattc     420
ctgggagtct actaccacaa gaacaacaag tcctggatgg agtctgagtt cagggtctac     480
tcctctgcca caactgtgac ctttgaatat gtgagccaac cattcctgat ggacttggag     540
ggcaagcagg gcaacttcaa gaacctgagg gagtttgtgt tcaagaacat tgatggctac     600
ttcaagattt acagcaaaca cacaccaatc aacctggtga gggacctgcc acagggcttc     660
tctgccttgg aaccactggt ggacctgcca attggcatca acatcaccag gttccagacc     720
ctgctggctc tgcacaggtc ctacctgaca cctggagact cctcctctgg ctggacagca     780
ggagcagcag cctactatgt gggctacctc caaccaagga ccttcctgct gaaatacaat     840
gagaatggca ccatcacaga tgctgtggac tgtgccctgg acccactgtc tgagaccaag     900
tgtaccctga atccttcac agtggagaag ggcatctacc agaccagcaa cttcagggtc     960
caaccaacag agagcattgt gaggtttcca aacatcacca acctgtgtcc atttggagag    1020
gtgttcaatg ccaccaggtt tgcctctgtc tatgcctgga acaggaagag gattagcaac    1080
tgtgtggctg actactctgt gctctacaac tctgcctcct tcagcacctt caagtgttat    1140
ggagtgagcc caaccaaact gaatgacctg tgtttcacca atgtctatgc tgactccttt    1200
gtgattaggg gagatgaggt gagacagatt gcccctggac aaacaggcaa gattgctgac    1260
tacaactaca aactgcctga tgacttcaca ggctgtgtga ttgcctggaa cagcaacaac    1320
ctggacagca aggtgggagg caactacaac tacctctaca gactgttcag gaagagcaac    1380
ctgaaaccat ttgagaggga catcagcaca gagatttacc aggctggcag cacaccatgt    1440
aatggagtgg agggcttcaa ctgttacttt ccactccaat cctatggctt ccaaccaacc    1500
aatggagtgg gctaccaacc atacagggtg gtggtgctgt cctttgaact gctccatgcc    1560
cctgccacag tgtgtggacc aaagaagagc accaacctgg tgaagaacaa gtgtgtgaac    1620
ttcaacttca atggactgac aggcacagga gtgctgacag agagcaacaa gaagttcctg    1680
```

```
ccattccaac agtttggcag ggacattgct gacaccacag atgctgtgag ggacccacag    1740
accttggaga ttctggacat cacaccatgt tcctttggag gagtgtctgt gattacacct    1800
ggcaccaaca ccagcaacca ggtggctgtg ctctaccagg atgtgaactg tactgaggtg    1860
cctgtggcta tccatgctga ccaacttaca ccaacctgga gggtctacag cacaggcagc    1920
aatgtgttcc agaccagggc tggctgtctg attggagcag agcatgtgaa caactcctat    1980
gagtgtgaca tcccaattgg agcaggcatc tgtgcctcct accagaccca gaccaacagc    2040
ccaaggaggg caaggtctgt ggcaagccag agcatcattg cctacacaat gagtctggga    2100
gcagagaact ctgtggctta cagcaacaac agcattgcca tcccaaccaa cttcaccatc    2160
tctgtgacca cagagattct gcctgtgagt atgaccaaga cctctgtgga ctgtacaatg    2220
tatatctgtg agacagcac agagtgtagc aacctgctgc tccaatatgg ctccttctgt    2280
acccaactta cagggctct gacaggcatt gctgtggaac aggacaagaa cacccaggag    2340
gtgtttgccc aggtgaagca gatttacaag acacctccaa tcaaggactt tggaggcttc    2400
aacttcagcc agattctgcc tgacccaagc aagccaagca gaggtccttc cattgaggac    2460
ctgctgttca caaggtgac cctggctgat gctggcttca tcaagcaata tggagactgt    2520
ctgggagaca ttgctgccag ggacctgatt tgtgcccaga gttcaatgg actgacagtg    2580 ctgcctccac tgctgacaga tgagatgatt gcccaataca cctctgccct gctggctggc    2640
accatcacct ctggctggac cttggagca ggagcagccc tccaaatccc atttgctatg    2700
cagatggctt acaggttcaa tggcattgga gtgacccaga atgtgctcta tgagaaccag    2760
aaactgattg ccaaccagtt caactctgcc attggcaaga ttcaggactc cctgtccagc    2820
acagcctctg ccctgggcaa actccaagat gtggtgaacc agaatgccca ggctctgaac    2880
accctggtga agcaactttc cagcaacttt ggagccatct cctctgtgct gaatgacatc    2940
ctgagcagac tggacaaggt ggaggctgag gtccagattg acagactgat tacaggcaga    3000
ctccaatccc tccaaaccta tgtgacccaa caacttatca gggctgctga gattagggca    3060
tctgccaacc tggctgccac caagatgagt gagtgtgtgc tgggacaaag caagagggtg    3120
gacttctgtg gcaagggcta ccacctgatg agttttccac agtctgcccc tcatggagtg    3180
gtgttcctgc atgtgaccta tgtgcctgcc caggagaaga acttcaccac agcccctgcc    3240
atctgccatg atggcaaggc tcactttcca agggaggag tgtttgtgag caatggcacc    3300
cactggtttg tgacccagag gaacttctat gaaccacaga ttatcaccac agacaacacc    3360
tttgtgtctg caactgtga tgtggtgatt ggcattgtga caacacagt ctatgaccca    3420 ctccaacctg aactggactc cttcaaggag gaactggaca atacttcaa gaaccacacc    3480 agccctgatg tggacctggg agacatctct ggcatcaatg cctctgtggt gaacatccag    3540
aaggagattg acagactgaa tgaggtggct aagaacctga atgagtccct gattgacctc    3600
caagaactgg gcaaatatga acaatacatc aagtggccac atcatcacca ccatcactaa    3660
```

<210> SEQ ID NO 18
<211> LENGTH: 1214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Phe Val Phe Leu Val Leu Leu Pro Leu Val Ser Ser Gln Cys Val

-continued

```
1               5                   10                  15
Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
            35                  40                  45

His Ser Thr Gln Asp Leu Phe Leu Pro Phe Phe Ser Asn Val Thr Trp
50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
                100                 105                 110

Lys Thr Gln Ser Leu Leu Ile Val Asn Asn Ala Thr Asn Val Val Ile
                115                 120                 125

Lys Val Cys Glu Phe Gln Phe Cys Asn Asp Pro Phe Leu Gly Val Tyr
            130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
                180                 185                 190

Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
            290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
            370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430
```

-continued

```
Val Ile Ala Trp Asn Ser Asn Leu Asp Ser Lys Val Gly Gly Asn
         435                 440                 445
Tyr Asn Tyr Leu Tyr Arg Leu Phe Arg Lys Ser Asn Leu Lys Pro Phe
450                 455                 460
Glu Arg Asp Ile Ser Thr Glu Ile Tyr Gln Ala Gly Ser Thr Pro Cys
465                 470                 475                 480
Asn Gly Val Glu Gly Phe Asn Cys Tyr Phe Pro Leu Gln Ser Tyr Gly
                485                 490                 495
Phe Gln Pro Thr Asn Gly Val Gly Tyr Gln Pro Tyr Arg Val Val Val
            500                 505                 510
Leu Ser Phe Glu Leu Leu His Ala Pro Ala Thr Val Cys Gly Pro Lys
        515                 520                 525
Lys Ser Thr Asn Leu Val Lys Asn Lys Cys Val Asn Phe Asn Phe Asn
530                 535                 540
Gly Leu Thr Gly Thr Gly Val Leu Thr Glu Ser Asn Lys Lys Phe Leu
545                 550                 555                 560
Pro Phe Gln Gln Phe Gly Arg Asp Ile Ala Asp Thr Thr Asp Ala Val
                565                 570                 575
Arg Asp Pro Gln Thr Leu Glu Ile Leu Asp Ile Thr Pro Cys Ser Phe
            580                 585                 590
Gly Gly Val Ser Val Ile Thr Pro Gly Thr Asn Thr Ser Asn Gln Val
        595                 600                 605
Ala Val Leu Tyr Gln Asp Val Asn Cys Thr Glu Val Pro Val Ala Ile
        610                 615                 620
His Ala Asp Gln Leu Thr Pro Thr Trp Arg Val Tyr Ser Thr Gly Ser
625                 630                 635                 640
Asn Val Phe Gln Thr Arg Ala Gly Cys Leu Ile Gly Ala Glu His Val
                645                 650                 655
Asn Asn Ser Tyr Glu Cys Asp Ile Pro Ile Gly Ala Gly Ile Cys Ala
            660                 665                 670
Ser Tyr Gln Thr Gln Thr Asn Ser Pro Arg Arg Ala Arg Ser Val Ala
        675                 680                 685
Ser Gln Ser Ile Ile Ala Tyr Thr Met Ser Leu Gly Ala Glu Asn Ser
        690                 695                 700
Val Ala Tyr Ser Asn Asn Ser Ile Ala Ile Pro Thr Asn Phe Thr Ile
705                 710                 715                 720
Ser Val Thr Thr Glu Ile Leu Pro Val Ser Met Thr Lys Thr Ser Val
                725                 730                 735
Asp Cys Thr Met Tyr Ile Cys Gly Asp Ser Thr Glu Cys Ser Asn Leu
            740                 745                 750
Leu Leu Gln Tyr Gly Ser Phe Cys Thr Gln Leu Asn Arg Ala Leu Thr
        755                 760                 765
Gly Ile Ala Val Glu Gln Asp Lys Asn Thr Gln Glu Val Phe Ala Gln
770                 775                 780
Val Lys Gln Ile Tyr Lys Thr Pro Pro Ile Lys Asp Phe Gly Gly Phe
785                 790                 795                 800
Asn Phe Ser Gln Ile Leu Pro Asp Pro Ser Lys Pro Ser Lys Arg Ser
                805                 810                 815
Phe Ile Glu Asp Leu Leu Phe Asn Lys Val Thr Leu Ala Asp Ala Gly
            820                 825                 830
Phe Ile Lys Gln Tyr Gly Asp Cys Leu Gly Asp Ile Ala Ala Arg Asp
        835                 840                 845
```

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
                915                 920                 925

Ser Ala Ile Gly Lys Ile Gln Asp Ser Leu Ser Ser Thr Ala Ser Ala
            930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
            995                 1000                1005

Thr Gln Gln Leu Ile Arg Ala Ala Glu Ile Arg Ala Ser Ala Asn
        1010                1015                1020

Leu Ala Ala Thr Lys Met Ser Glu Cys Val Leu Gly Gln Ser Lys
        1025                1030                1035

Arg Val Asp Phe Cys Gly Lys Gly Tyr His Leu Met Ser Phe Pro
        1040                1045                1050

Gln Ser Ala Pro His Gly Val Val Phe Leu His Val Thr Tyr Val
        1055                1060                1065

Pro Ala Gln Glu Lys Asn Phe Thr Thr Ala Pro Ala Ile Cys His
        1070                1075                1080

Asp Gly Lys Ala His Phe Pro Arg Glu Gly Val Phe Val Ser Asn
        1085                1090                1095

Gly Thr His Trp Phe Val Thr Gln Arg Asn Phe Tyr Glu Pro Gln
        1100                1105                1110

Ile Ile Thr Thr Asp Asn Thr Phe Val Ser Gly Asn Cys Asp Val
        1115                1120                1125

Val Ile Gly Ile Val Asn Asn Thr Val Tyr Asp Pro Leu Gln Pro
        1130                1135                1140

Glu Leu Asp Ser Phe Lys Glu Glu Leu Asp Lys Tyr Phe Lys Asn
        1145                1150                1155

His Thr Ser Pro Asp Val Asp Leu Gly Asp Ile Ser Gly Ile Asn
        1160                1165                1170

Ala Ser Val Val Asn Ile Gln Lys Glu Ile Asp Arg Leu Asn Glu
        1175                1180                1185

Val Ala Lys Asn Leu Asn Glu Ser Leu Ile Asp Leu Gln Glu Leu
        1190                1195                1200

Gly Lys Tyr Glu Gln His His His His His His
        1205                1210

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic

```
                        -continued
        oligonucleotide

<400> SEQUENCE: 19
gatgcgcaca gcccacgtgt                                          20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 20
acagtgtggc acggaagcat                                          20
```